United States Patent [19]

Barriere et al.

[11] Patent Number: 4,755,599
[45] Date of Patent: Jul. 5, 1988

[54] 3-PHENYL-2-PROPENEAMINE DERIVATIVES, THEIR PREPARATION AND COMPOSITION CONTAINING THEM

[75] Inventors: Jean-Claude Barriere, Massy; Jean-Pierre Corbet, Ecully; Claude Cotrel, Paris; Daniel Farge, Thiais; Jean-Marc Paris, Vaires S/Marne, all of France

[73] Assignee: Rhone-Poulenc Sante, Courbevoie, France

[21] Appl. No.: 10,558

[22] Filed: Feb. 3, 1987

Related U.S. Application Data

[62] Division of Ser. No. 702,088, Feb. 15, 1985, Pat. No. 4,686,309.

[30] Foreign Application Priority Data

Feb. 16, 1984 [FR] France ................................ 8402338

[51] Int. Cl.$^4$ ................ C07D 279/04; C07D 401/06; C07D 277/04; C07D 275/02; C07D 205/04; C07D 207/08; C07D 223/04; C07C 149/24
[52] U.S. Cl. .................................... 540/544; 540/553; 540/597; 540/609; 540/610; 544/53; 544/55; 544/59; 544/60; 544/88; 544/96; 544/158; 544/170; 544/333; 544/335; 544/360; 544/401; 546/193; 546/232; 546/246; 546/248; 546/334; 548/146; 548/214; 548/215; 548/240; 548/300; 548/356; 548/518; 548/566; 548/570; 564/340; 564/355; 564/360; 564/361
[58] Field of Search .............. 564/340, 355, 360, 361; 540/544, 553, 597, 609, 610; 544/53, 55, 59, 60, 88, 96, 158, 170, 333, 335, 360, 401; 546/193, 232, 246, 248, 334; 548/146, 214, 215, 240, 300, 356, 518, 566

[56] References Cited

U.S. PATENT DOCUMENTS 3,978,129  8/1976  Welstead .............................. 564/355
4,018,845  4/1977  Molloy et al. ....................... 564/355
4,056,630  11/1977  Clark ................................... 514/653

OTHER PUBLICATIONS

Sundberg, R. J. et al. *J. of Organic Chemistry*, vol. 46, No. 18, (1981), pp. 3730–3732.

*Primary Examiner*—Glennon H. Hollrah
*Assistant Examiner*—John A. Sopp

*Attorney, Agent, or Firm*—Stevens, Davis, Miller & Mosher

[57] ABSTRACT

The invention provides compounds of formula:

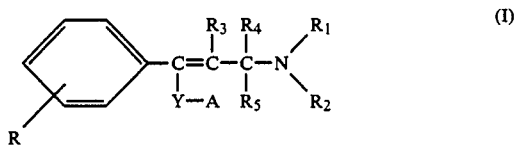

(I)

in which
$R$=H, halogen, alkyl, alkyloxy, alkythio, $NH_2$, alkylamino, dialkylamino or $CF_3$, $R_3$=H or alkyl,
either $R_4$ and $R_5$=H and $R_1$ and $R_2$=H or alkyl, optionally substituted by alkenyl (2 to 4 C) or alternatively $R_1$ and $R_2$ form together a saturated heterocyclic ring containing 4 to 7 ring members and optionally containing another heteroatom such as O, S or N optionally substituted by alkyl,
or $R_4$=H, $R_1$=H or alkyl and $R_2$ and $R_5$ together form an alkylene (3 to 4 C) radical and
(i) either A=alkyl or phenyl which is unsubstituted or substituted by one or two substituents chosen from halogen, alkyl, alkyloxy, alkylthio, $NH_2$, alkylamino, dialkylamino, $NO_2$ or $CF_3$ or alternatively A=pyridyl, benzyl or cycloalkyl (3 to 6 C), Y=S, SO or $SO_2$ or a radical:

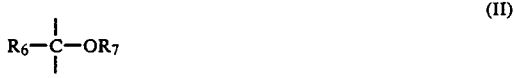

(II)

in which $R_6$=H or alkyl and $R_7$=H or alkylcarbonyl, alkyloxycarbonyl, alkylaminocarbonyl or benzoyl, optionally substituted by one or two halogen, alkyl, alkyloxy, alkylthio, $NH_2$, alkylamino, dialkylamino, $NO_2$ or $CF_3$ groups,
(ii) or Y and A together form a 1-hydroxycycloalkyl radical, the ring of which contains 5 or 6 C, optionally joined to a benzene ring,
it being understood that the alkyl radicals and alkyl parts contains 1 to 4 C as a straight or branched chain, and that the invention relates to all the possible geometric and optical isomers as well as their mixtures.

These compounds are useful as antidepressants.

1 Claim, No Drawings

3-PHENYL-2-PROPENEAMINE DERIVATIVES, THEIR PREPARATION AND COMPOSITION CONTAINING THEM

This is a division of application Ser. No. 702,088 filed Feb. 15, 1985, now U.S. Pat. No. 4,686,309.

The present invention relates to phenylpropeneamine derivatives and their preparation and to pharmaceutical compositions containing the same.

More particularly, the invention provides the 3-phenyl-2-propeneamine derivatives of formula:

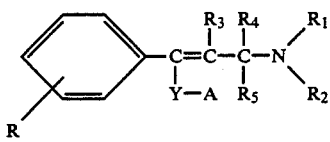

in which

R denotes hydrogen, halogen, alkyl, alkyloxy, alkylthio, amino, alkylamino, dialkylamino or trifluoromethyl, $R_3$ denotes hydrogen or alkyl;

either $R_4$ and $R_5$ each denote hydrogen and $R_1$ and $R_2$, which are identical or different, each denote hydrogen or alkyl which is unsubstituted or substituted by alkenyl of 2 to 4 carbon atoms, or $R_1$ and $R_2$ form together with the nitrogen atom to which they are linked a saturated heterocyclic radical of 4 to 7 ring atoms and optionally containing another heteroatom such as oxygen, sulphur or nitrogen which is unsubstituted or substituted by alkyl, or $R_4$ denotes hydrogen, $R_1$ denotes hydrogen or alkyl and $R_2$ and $R_5$ form together an alkylene radical of 3 or 4 carbon atoms and either (i) A denotes alkyl or phenyl which is unsubstituted or substituted by one or two substituents chosen from halogen, alkyl, alkyloxy, alkylthio, amino, alkylamino, dialkylamino, nitro and trifluoromethyl or A denotes pyridyl, benzyl, or cycloalkyl of 3 to 6 carbon atoms and Y denotes sulphur, sulphinyl or sulphonyl or a radical of formula:

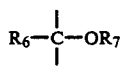

in which $R_6$ denotes hydrogen or alkyl and $R_7$ denotes hydrogen, alkylcarbonyl, alkyloxycarbonyl, alkylaminocarbonyl or benzoyl which is unsubstituted or substituted by one or two substituents chosen from halogen, alkyl, alkyloxy, alkylthio, amino, alkylamino, dialkylamino, nitro and trifluoromethyl or (ii) Y and A together form a 1-hydroxycycloalkyl radical the ring of which contains 5 or 6 carbon atoms, optionally coupled to a benzene ring, it being understood that in the preceding definitions and in those which follow, the alkyl radicals and alkyl parts contain 1 to 4 carbon atoms as a straight or branched chain and that the invention relates to all the possible geometric and optical isomers and their mixtures.

According to the invention, the compound of formula (I) in which Y denotes a radical of formula (II) in which $R_6$ is defined as previously and $R_7$ denotes hydrogen and A, R, $R_1$ and $R_2$ are defined as previously, except that $R_1$ and/or $R_2$ is not hydrogen, and which are in the Z configuration, are prepared by the reaction of a compound of formula:

in which A and $R_6$ are as defined previously, with a carbanion of general formula:

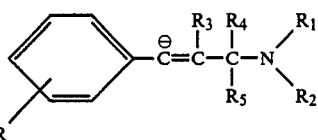

in which the symbols are as defined previously, except that $R_1$ and/or $R_2$ is not hydrogen.

The reaction is generally carried out in an inert organic solvent such as hexane, pentane, ethyl ether, 1,2-dimethoxyethane or tetrahydrofuran or a mixture of these solvents, at a temperature in the region of −30° C.

The carbanion of formula (IV) can be obtained according to one of the following methods, depending on the nature of the radicals:

(A) When R is defined as previously, except for denoting halogen or trifluoromethyl, and $R_1$ and $R_2$ are defined as previously, except that $R_1$ and/or $R_2$ is not hydrogen, it may be obtained by reacting an organometallic base with a compound of general formula:

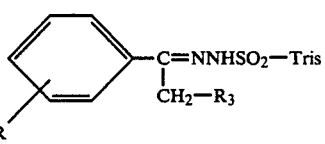

in which R is defined as previously, but is not halogen or trifluoromethyl, and the symbol Tris denotes the 2,4,6-triisopropylphenyl radical, followed by the reaction of a product of formula:

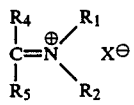

in which the symbols are defined as previously, except that $R_1$ and/or $R_2$ is not hydrogen, and $X^\ominus$ denotes a halide (preferably iodide)ion, to obtain an intermediate of formula:

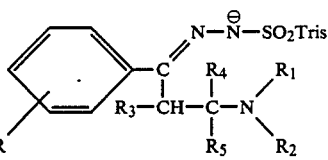

in which the symbols are defined as previously, except that R is not halogen or trifluoromethyl and $R_1$ and/or $R_2$ is not hydrogen, and the symbol Tris is defined as previously, this intermediate of general formula (VII) being then treated with an organometallic base to give, after fragmentation, the corresponding carbanion of general formula (IV).

In practice, it is advantageous to dissolve the compound of formula (V) in an inert solvent such as 1,2- dimethoxyethane, to treat the solution obtained with two equivalents of butyllithium dissolved in hexane, operating at a temperature of between −70° and −78° C., to condense the product of formula (VI) at a temperature in the region of −50° C., to treat the intermediate of general formula (VII) which is obtained with one equivalent of butyllithium dissolved in hexane at a temperature of between −70° and −78° C. and to allow the temperature to rise to about 0° C. In this case, the corresponding carbanion of general formula (IV) is obtained in solution in a mixture of 1,2-dimethoxyethane and hexane.

The products of general formula (V) may be prepared by reaction of 2,4,6-triisopropylbenzenesulphonylhydrazine with a product of general formula:

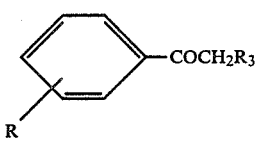

in which R and $R_3$ are defined as previously, except for R denoting a halogen atom or a trifluoromethyl radical, by proceeding according to the method described by M. F. Lipton and R. H. Shapiro, *J. Org. Chem.* 43, 1409 (1978).

(B) When the symbols R, $R_1$, $R_2$ and $R_3$ are defined as in the general formula (IV), and $R_4$ and $R_5$ denote a hydrogen atom, the carbanion may be obtained by reaction of an organometallic base with a product of general formula:

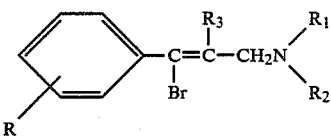

in which the symbols have the definition given for the carbanion of general formula (IV).

In practice, it is advantageous to employ butyllithium dissolved in hexane as an organometallic base and to carry out the reaction in an inert organic solvent such as a hydrocarbon (for example pentane) or an ether (for example ethyl ether) at a temperature of between −78° and −10° C. In this case, the carbanion of general formula (IV) is obtained in solution in a mixture of pentane and hexane or in a mixture of ethyl ether and hexane.

The products of general formula (IX) can be prepared starting from a product of general formula:

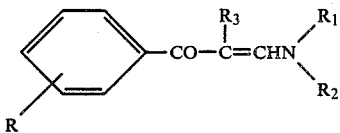

in which R, $R_1$, $R_2$ and $R_3$ have the definitions given previously for the carbanion of general formula (IV), by successive reaction with phosphorus oxybromide, methanol and an alkali metal borohydride such as sodium cyanoborohydride.

The operation is generally carried out in an organic solvent such as methylene chloride, at a temperature of between 0° and 10° C.

The products of general formula (X) can be prepared by employing or modifying the method described by H. Meerwein, W. Florian, N. Schon and G. Stopp, *Ann. Chem.*, 641, 1, (1961).

When R is defined as previously, except for denoting a halogen atom or a trifluoromethyl radical, and $R_1$ and/or $R_2$ are defined as previously, except for denoting a hydrogen atom, the carbanion can be obtained by reaction of an organometallic base with a product of general formula:

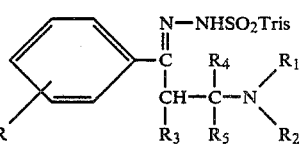

in which R, $R_1$, $R_2$, $R_3$, $R_4$ and $R_5$ are defined as previously, except for R denoting a halogen atom or a trifluoromethyl radical and for $R_1$ and/or $R_2$ denoting a hydrogen atom, and the symbol Tris is defined as previously in the general formula (V), to obtain an intermediate of general formula:

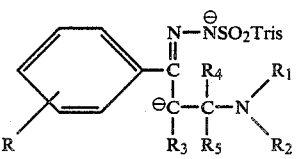

in which R, $R_1$, $R_2$, $R_3$, $R_4$, $R_5$ and Tris have the corresponding definitions, this intermediate then being fragmented to give the corresponding carbanion of general formula (IV).

In practice the organometallic base employed is n-butyllithium or tert.-butyllithium dissolved in an aliphatic hydrocarbon such as hexane or pentane, and the reaction is carried out in an inert organic solvent such as 1,2-dimethoxyethane at a temperature of between −78° and −70° C., and then the temperature is allowed to rise to about 0° C. In this case, the corresponding carbanion of general formula (IV) is obtained in solution in a mixture of 1,2-dimethoxyethane and hexane or 1,2-dimethoxyethane and pentane.

The products of general formula (XI) may be prepared by reaction of 2,4,6-triisopropylbenzenesulphonylhydrazine with a product of general formula:

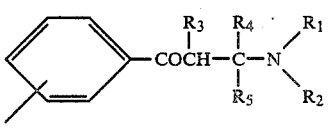

in which R, $R_1$, $R_2$, $R_3$, $R_4$ and $R_5$ are defined as previously, except for R denoting a halogen atom or a trifluoromethyl radical and for $R_1$ and/or $R_2$ denoting a hydrogen atom.

The operation is generally carried out in an organic solvent such as an alcohol containing dissolved hydrogen chloride.

The products of general formula (XIII) can be prepared by employing or modifying the method described by C. E. Maxwell, *Org. Syntheses*, Coll. Vol. III, John Wiley & Sons, London (1955) page 305.

According to the invention, the products of general formula (I) in which Y denotes a radical of general formula (II) in which $R_6$ and $R_7$ denote a hydrogen atom, A is defined earlier under (i), $R_1$ denotes a hydrogen atom, $R_2$ denotes a hydrogen atom or an alkyl radical optionally substituted by an alkenyl radical containing 2 to 4 carbon atoms, R denotes a hydrogen atom, $R_3$ is defined as previously and $R_4$ and $R_5$ denote a hydrogen atom, and which are in the Z configuration, may be prepared by opening the dihydrofuran ring in a product of general formula:

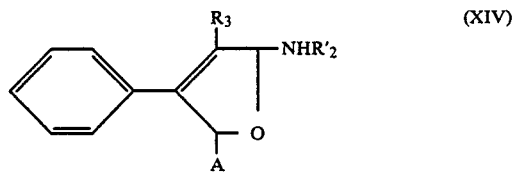
(XIV)

in which A is defined as previously under (i) and $R'_2$ denotes an alkyl radical optionally substituted by an alkenyl radical containing 2 to 4 carbon atoms and $R_3$ is defined as previously.

Generally, the opening of the dihydrofuran ring is carried out with the aid of an alkali metal borohydride such as sodium borohydride in a mixture of water and alcohol, for example methanol-water, at a temperature of between 0° and 20° C., preferably at a temperature in the region of 5° C.

When the intention is to use this process to obtain a product of general formula (I) in which Y denotes a radical of general formula (II) in which $R_6$ and $R_7$ denote a hydrogen atom, A is defined as previously under (i), R, $R_1$, $R_2$, $R_4$ and $R_5$ denote a hydrogen atom and $R_3$ is defined as previously, and which are in the Z configuration, it is necessary to start from a product of general formula (XIV) in which $R'_2$ denotes an alkyl radical optionally substituted by an alkenyl radical containing 2 to 4 carbon atoms, and then to remove the said radical according to a known method, for example the method of D. Picq, M. Cottin, D. Anker and H. Pacheco, *Tet. Letters* (1983), 1399.

The products of general formula (XIV) can be prepared by reaction of a product of general formula (XV), in equilibrium with its tautomeric form,

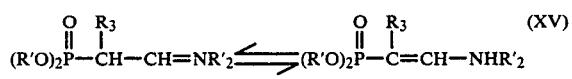
(XV)

in which $R'_2$ denotes an alkyl radical optionally substituted by an alkenyl radical containing 2 to 4 carbon atoms and R' denotes an alkyl (preferably ethyl) radical with a product of general formula:

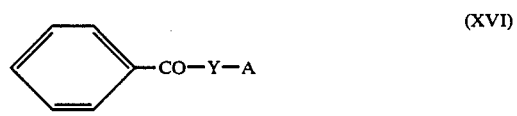
(XVI)

in which Y denotes a radical of general formula (II) in which $R_6$ and $R_7$ denote a hydrogen atom and A is defined as previously under (i).

The operation is generally carried out in an organic solvent such as tetrahydrofuran in the presence of a condensing agent such as an alkali metal hydride, at a temperature of between 20° and 100° C., preferably at a temperature in the region of 60° C.

The products of general formula (XV) can be prepared according to the method described by N. D. Dawson and A. Burger, *J. Am. Chem. Soc.* 74, 5312, (1952).

The products of general formula (XVI) can be prepared by employing or modifying the methods of L. R. Krepski, S. M. Heilmann and J. K. Rasmussen, *Tet. Letters*, 4075, (1983) or of R. E. Koenigkramer and H. Zimmer, *Tet. Letters*, 1017, (1980).

According to the invention, the products of general formula (I) in which Y denotes a sulphur atom, $R_4$ and $R_5$ denote a hydrogen atom, A is defined as previously under (i) and the remaining symbols are defined as previously, except for $R_1$ and/or $R_2$ denoting a hydrogen atom, and which are in the Z or E configuration, can be prepared by reaction of a mercaptan of general formula:

A—SH   (XVII)

in which A is defined as previously under (i) with a product of general formula:

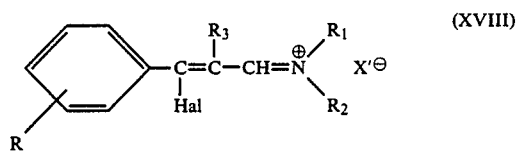
(XVIII)

in which R, $R_1$, $R_2$, and $R_3$ are defined as previously, except for $R_1$ and/or $R_2$ denoting a hydrogen atom, Hal denotes a halogen atom such as chlorine or bromine, and $X'^{\ominus}$ denotes any anion such as halide, chlorate, perchlorate, phosphate or fluoroborate, followed by a reduction of the intermediate obtained, of general formula:

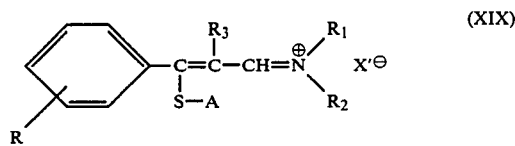
(XIX)

in which the symbols have the corresponding meanings.

The reaction of the product of formula (XVII) with the product of formula (XVIII) is generally carried out in a chlorinated solvent, an alcohol or an ether, or a mixture of these solvents, in the presence of an acid-acceptor such as triethylamine, at a temperature of between 0° and 20° C.

The reduction of the intermediate of general formula (XIX) is generally carried out with the aid of an alkali metal borohydride such as sodium borohydride or sodium cyanoborohydride, in the solvent in which the condensation of the product of general formula (XVII) with the product of general formula (XVIII) has been carried out.

The products of general formula (XVIII) can be prepared by reaction of a phosphorus oxyhalide with a product of general formula (X) in which R, $R_1$ and $R_2$ are defined as previously, except for $R_1$ and/or $R_2$ denoting a hydrogen atom.

The operation is generally carried out in a chlorinated solvent such as methylene chloride, at a temperature of between 0° and 20° C.

In order to carry out the reaction consisting in reacting the product of general formula (XVII) with the product of general formula (XVIII), it is not necessary for the product of general formula (XVIII) to have been isolated. After the product of general formula (XVIII) has been prepared as stated above, it suffices to add the product of general formula (XVII) and an acid-acceptor to the reaction mixture and to continue the reaction at a temperature of between 0° and 20° C., and then to reduce in situ the intermediate of general formula (XIX) as set out above.

According to the invention, the products of general formula (I) in which Y denotes a sulphur atom, $R_4$ and $R_5$ denote a hydrogen atom, A is defined as previously under (i) and the remaining symbols are defined as previously, and which are in the Z or E configuration, can also be prepared by reaction of ammonia or an amine of general formula:

 (XX)

in which $R_1$ and $R_2$ are defined as previously, with an aldehyde of general formula:

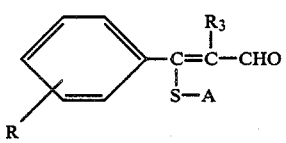 (XXI)

in which A is defined as previously under (i) and R and $R_3$ are defined as previously, and which is in the Z or E configuration.

The operation is generally carried out in an organic solvent such as an alcohol, such as methanol, in the presence of an alkali metal borohydride such as sodium cyanoborohydride and of molecular sieves, at a temperature in the region of 20° C.

The products of general formula (XXI) can be prepared by reaction of a mercaptan of general formula (XVII) defined as previously with a product of general formula:

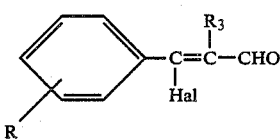 (XXII)

in which R and $R_3$ are defined as previously and Hal denotes a halogen atom such as chlorine or bromine and which is in the E or Z configuration.

The operation is generally carried out in an organic solvent such as methylene chloride in the presence of an acid-acceptor such as triethylamine, at a temperature of between 0° and 20° C.

The product of general formula (XXII) can be prepared by employing or modifying the method of C. M. Beaton, N. B. Chapman and K. Klarke, *J. Chem. Soc.* Perkin I, 2355, (1976).

According to the invention, the products of general formula (I) in which Y denotes a radical of general formula (II) in which $R_7$ denotes a hydrogen atom or alternatively Y is defined as under (ii) and the remaining symbols are defined as previously, and which are in the E configuration, can be prepared by reaction of an organomagnesium derivative of general formula:

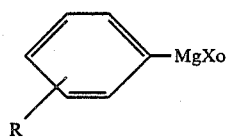 (XXIII)

in which R is defined as previously and Xo denotes a halogen atom (preferably bromine) with a product of general formula:

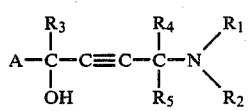 (XXIV)

in which the symbols are defined as previously.

The operation is carried out according to methods known to those skilled in the art for reacting an organomagnesium derivative with an acetylene derivative without affecting the remainder of the molecule.

When $R_1$ and/or $R_2$ denote a hydrogen atom, it is obvious to the person skilled in the art that the corresponding amine function will need to be protected in the product of general formula (XXIV) before reaction with the organomagnesium derivative of formula (XXIII). It is possible to employ any blocking means known to the person skilled in the art to protect a primary or secondary amine, which does not affect the remainder of the molecule and which can be removed subsequently.

The products of general formula (XXIV) can be prepared by reaction of a product of general formula:

 (XXV)

in which A and $R_3$ are defined as previously with a propargylamine of general formula:

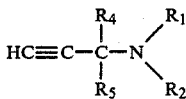 (XXVI)

in which $R_1$, $R_2$, $R_4$ and $R_5$ are defined as previously, except for $R_1$ and $R_2$ denoting, together or separately, a hydrogen atom.

The reaction is generally carried out in an inert organic solvent such as 1,2-dimethoxyethane, at a temperature of between $-40°$ and 0° C., after the propargylamine of general formula (XXVI) has been metalated by any known means. The metalation can be carried out, for example, with the aid of an organometallic base such as n-butyllithium dissolved in hexane at a temperature in the region of $-70°$ C.

The products of general formula (XXVI) can be prepared by reaction of an amine of general formula (XX)

defined as previously with propargyl bromide by employing or modifying the method of M. Gaudemar, *Ann. Chim.* (France) 13, 161, (1956).

According to the invention, the products of general formula (I) in which Y denotes a radical of general formula (II) in which $R_7$ denotes an alkylcarbonyl, alkoxycarbonyl or benzoyl radical optionally substituted by one or two substituents chosen from halogen atoms and alkyl, alkyloxy, alkylthio, amino, alkylamino, dialkylamino, nitro or trifluoromethyl radicals, and the remaining symbols are defined as previously, can be obtained by reaction of a product of general formula:

$$R'_7X_1 \quad \text{(XXVII)}$$

in which $R'_7$ denotes an alkylcarbonyl, alkoxycarbonyl or benzoyl radical optionally substituted by one or two substituents chosen from halogen atoms and alkyl, alkyloxy, alkylthio, amino, alkylamino, dialkylamino, nitro or trifluoromethyl radicals and $X_1$ denotes a reactive ester residue such as a halide with a product of general formula (I) in which Y denotes a radical of general formula (II) in which $R_7$ denotes a hydrogen atom and the remaining symbols are defined as previously, that is to say a product of general formula:

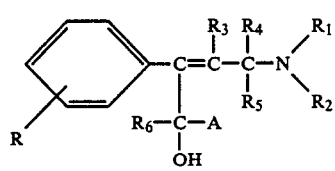

(XXVIII)

The operation is carried out using any method known to those skilled in the art for acylating a secondary or tertiary alcohol, for example by working in pyridine at a temperature of between 0° and 50° C., or in an inert solvent such as a chlorinated solvent, in the presence of an acid-acceptor when $X_1$ denotes a halogen atom.

It is clear to the person skilled in the art that, when $R_1$ and/or $R_2$ denote a hydrogen atom, it is necessary to block the corresponding amine function before reacting the product of general formula (XXVII) with the product of general formula (XXVIII). The amine function is then liberated after the process has been carried out. Blocking of the amine can be carried out, for example, in the form of a tert.-butyloxycarbonyl radical, readily capable of cleavage by known methods without affecting the radical $R_7$ introduced into the molecule by using the present procedure.

According to the invention, the products of general formula (I) in which Y denotes a sulphur atom or a radical or general formula (II) defined as previously, $R_4$ and $R_5$ denote a hydrogen atom and the remaining symbols are defined as previously, and which are in the E or Z configuration, can be prepared by reaction of ammonia, an amine-precursor or an amine of general formula (XX) with a product of general formula:

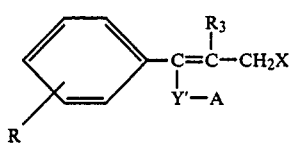

(XXIX)

in which A is defined as previously under (i) R and $R_3$ are defined as previously and
(a) either X denotes a chlorine atom and Y' denotes a sulphur atom or a radical of general formula (II) in which $R_6$ is defined as previously and $R_7$ denotes an alkyloxycarbonyl radical,
(b) or X denotes a bromine atom and Y' denotes a sulphur atom, and which is in the E or Z configuration, optionally followed by a hydrolysis when the intention is to obtain the product of general formula (I) in which Y denotes a radical of general formula (II) in which $R_7$ denotes a hydrogen atom, $R_4$ and $R_5$ denote a hydrogen atom and the remaining symbols are defined as previously.

The operation is generally carried out in an organic solvent such as an alcohol, such as ethanol or dimethylformamide, by operating under pressure if appropriate, at a temperature which may be between 0° and 100° C.

The subsequent optional hydrolysis can be carried out by any means known to those skilled in the art for removing an alkylcarbonyl, alkyloxycarbonyl, or benzoyl radical optionally substituted by one or two substituents chosen from halogen atoms and alkyl, alkyloxy, alkylthio, amino, alkylamino, dialkylamino, nitro or trifluoromethyl radicals or alkylaminocarbonyl employed to block an alcohol function. It is thus possible to operate in a solvent such as an alcohol in the presence of a base, such as sodium hydroxide or an alkali metal carbonate.

An amine-precursor as employed in the present method is understood to mean a product such as sodium azide which, after condensation with the product of general formula (XXIX) can produce the required amine by a subsequent operation which is known to those skilled in the art; in the case of sodium azide, the product of its condensation with the product of general formula (XXIX) is treated with 1,3-propanedithiol in the presence of an acid-acceptor such as triethylamine.

The products of general formula (XXIX) defined as previously under (a) can be obtained by reaction of an alkyl chloroformate with a product of general formula:

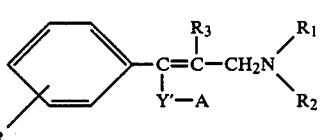

(IA)

in which R, $R_1$, $R_2$, $R_3$ and A are defined as previously and Y' denotes a sulphur atom or a radical of general formula (II) in which $R_6$ and $R_7$ are defined as previously and which is in the E or Z configuration.

The operation is generally carried out in an inert organic solvent such as an aromatic hydrocarbon, such as benzene or toluene, or a chlorinated solvent such as carbon tetrachloride, at a temperature of between 60° C. and the reflux temperature of the reaction mixture.

The products of general formula (XXIX) defined as previously under (b) can be obtained by reaction of cyanogen bromide with a product of general formula ($I_A$) in which R, $R_1$, $R_2$, $R_3$ and A have the corresponding meanings and Y' denotes a sulphur atom, and which is in the E or Z configuration.

The operation is generally carried out in a chlorinated solvent such as methylene chloride or chloroform, at a temperature of between 0° and 60° C.

The products of general formula (I₄) which are products according to the invention can be prepared by one of the methods described earlier.

According to the invention, the products of general formula (I) in which Y denotes a radical of general formula (II) in which R₇ denotes an alkylaminocarbonyl radical and the remaining symbols are defined as previously may be obtained by reaction of an isocyanate of general formula:

$$O=C=N-R''_7 \quad (XXX)$$

in which R''₇ denotes an alkyl radical with a product of general formula (I) in which Y denotes a radical of general formula (II) in which R₇ denotes a hydrogen atom and the remaining symbols are defined as previously, that is to say a product of general formula (XXVIII).

The operation is carried out by any method known to the person skilled in the art for preparing a carbamate from an isocyanate and an alcohol, for example by working in a chlorinated solvent such as chloroform at a temperature of between 0° C. and the reflux temperature of the reaction mixture.

It is obvious to the person skilled in the art that, when R1 and/or R2 denotes a hydrogen atom, it is necessary to block the corresponding amine function before reacting the product of general formula (XXX) with the product of general formula (XXVIII). The amine function is then liberated after the process has been carried out. Blocking of the amine may be, for example, in the form of a tert.-butyloxycarbonyl radical, readily capable of cleavage according to the known methods without affecting the radical R₇ introduced into the molecule using the present procedure.

According to the invention, the products of general formula (I) in which Y denotes a sulphinyl or sulphonyl radical and the remaining symbols are defined as previously can be prepared by oxidation of a product of general formula (I) in which Y denotes a sulphur atom and the remaining symbols are defined as previously, that is to say a product of general formula:

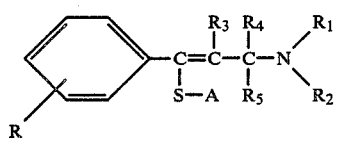

(XXXI)

The oxidation can be carried out by employing an agent which is generally employed to convert a sulphide to a sulphoxide or to a sulphone, by operating in a suitable solvent, without affecting the remainder of the molecule. For example, it is possible to employ hydrogen peroxide in acetone or acetic acid, an alkali metal periodate in an alcohol or acetonitrile, a carboxylic peroxyacid (peracetic, perbenzoic, m-chloroperbenzoic, p-nitroperbenzoic or perphthalic acid) in an ether (dioxane, tetrahydrofuran), or a chlorinated solvent (methylene chloride, dichloroethane), acetic acid or a mixture of these solvents.

When the intention is to produce the sulphoxide, that is to say the product of general formula (I) in which Y denotes a sulphinyl radical, it is particularly advantageous to work in methylene chloride in the presence of two equivalents of oxidising agent (preferably m-chloroperbenzoic acid) at a temperature in the region of 0° C., preferably in the presence of an equivalent of an inorganic acid.

When the intention is to produce the sulphone, that is to say the product of general formula (I) in which Y denotes a sulphonyl radical, it is particularly advantageous to work in the presence of at least 3 equivalents of oxidising agent at a temperature of between 20° C. and the reflux temperature of the reaction mixture.

It is obvious to the person skilled in the art that each time that one of the procedures set out above employs an organometallic derivative and reactant product molecules containing an amino function, the latter must be protected beforehand. For this purpose, the procedure follows the methods known to those skilled in the art. For example, the amino function can be protected by means of a labile silyl derivative which is readily removed when the reaction has ended.

The new products of general formula (I) can be purified by the usual methods such as crystallization, chromatography or successive extractions in an acidic and basic medium.

When the products of general formula (I) or their intermediates which are mentioned in the present description exist in E and Z forms as a mixture in the reaction medium, their separation can be carried out by any means known to the person skilled in the art, particularly by chromatography.

The new products of general formula (I) can be optionally converted into salts of addition with acids, by reaction with an acid in an organic solvent such as an alcohol, a ketone, an ester or a chlorinated solvent; the salt which is formed precipitates, optionally after its solution has been concentrated; it is isolated by filtration or decantation.

The new products of general formula (I) and their salts exhibit interesting pharmacological properties which make them useful as antidepressants.

They have been shown to be active particularly in the test for antagonist action against tetrabenazine-induced depression in the mouse at dosages of between 1 and 100 mg/kg by oral route.

Their lethal dose LD₅₀ is generally between 50 and 900 mg/kg by oral route.

Those of special importance are the products of general formula (I) in which R denotes a hydrogen, halogen, alkyl, alkyloxy, alkylthio, amino, alkylamino, dialkylamino or trifluoromethyl, R₃ denotes hydrogen or alkyl, and either R₄ and R₅ denote hydrogen and R₁ and R₂ which are identical or different, each denote hydrogen or alkyl optionally substituted by an alkenyl radical containing 2 to 4 carbon atoms, or R₁ and R₂ form together with the nitrogen atom to which they are linked a saturated heterocyclic radical containing 4 to 7 ring atoms (preferably 5 or 6 ring members), or R₄ denotes hydrogen, R₁ denotes hydrogen or alkyl and R₂ and R₅ together form an alkylene radical containing 3 or 4 carbon atoms (preferably 3 carbon atoms), and either (i) A denotes alkyl or phenyl which is unsubstituted or substituted by one or two substituents chosen from halogen, alkyl, alkyloxy and trifluoromethyl radicals, or A denotes pyridyl, benzyl or cycloalkyl containing 3 to 6 carbon atoms, Y denotes sulphur, sulphinyl, or a radical of formula:

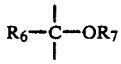
(II)

in which R₆ denotes hydrogen or alkyl and R₇ denotes hydrogen, alkylcarbonyl, alkyloxycarbonyl, benzoyl or alkylaminocarbonyl, or (ii) Y and A together form a 1-hydroxycycloalkyl radical the ring of which contains 5 or 6 carbon atoms, optionally combined with a benzene ring, in the Z or E form, it being understood that in the preceding definitions the alkyl radicals and alkyl parts contain 1 to 4 carbon atoms each, as a straight or branched chain.

Those of more particular importance are the products of general formula (I) in which R denotes hydrogen, halogen, alkyl, alkyloxy, alkylthio, amino, alkylamino, dialkylamino or trifluoromethyl, R₃ denotes hydrogen, R₄ and R₅ denote hydrogen, and R₁ and R₂, which are identical or different, each denote hydrogen, or alkyl optionally substituted by an alkenyl radical of 2 to 4 carbon atoms; and A denotes alkyl or phenyl, which is unsubstituted or substituted by one or two substituents chosen from halogen and alkyl, or alternatively A denotes pyridyl or cycloalkyl of 3 to 6 carbon atoms, Y denotes sulphur atom, or a radical of formula:

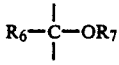
(II)

in which R₆ denotes hydrogen and R₇ denotes hydrogen or alkylcarbonyl, in the Z form, it being understood that in the preceding definitions the alkyl radicals and alkyl parts contain 1 to 4 carbon atoms as a straight or branched chain.

The following products are of very special interest:
4-dimethylamino-1,2-diphenyl-2-buten-1-ol (Z)
4-methylamino-1,2-diphenyl-2-buten-1-ol (Z)
1-(3-fluorophenyl)-4-dimethylamino-2-phenyl-2-buten-1-ol (Z)
1-(3-chlorophenyl)-4-dimethylamino-2-phenyl-2-buten-1-ol (Z)
1-(3-bromophenyl)-4-dimethylamino-2-phenyl-2-buten-1-ol (Z)
4-dimethylamino-1-(2-methylphenyl)-2-phenyl-2-buten-1-ol (Z)
4-amino-1,2-diphenyl-2-buten-1-ol (Z)
3-(2-chlorophenylthio)-1-dimethylamino-3-phenyl-2-propene (Z)
2-(3-chlorophenyl)-1-(3-fluorophenyl)-4-dimethylamino-2-buten-1-ol (Z)
2-(3-chlorophenyl)-4-dimethylamino-1-phenylthio-1-propene (Z)
1-(3-fluorophenyl)-4-methylamino-2-phenyl-2-buten-1-ol (Z)
3-amino-1-phenyl-1-phenylthio-1-propene (Z)
1-(4-chlorophenyl)-4-dimethylamino-2-phenyl-2-buten-1-ol (Z)
1-(4-bromophenyl)-4-dimethylamino-2-phenyl-2-buten-1-ol (Z)
4-acetoxy-1-dimethylamino-3,4-diphenyl-2-butene (Z)
4-allylamino-1,2-diphenyl-2-buten-1-ol (Z)
1-(2-chlorophenyl)-4-dimethylamino-2-phenyl-2-buten-1-ol (Z)
3-(4-fluorophenylthio)-3-phenyl-2-propene (Z)
1-(2-fluorophenyl)-2-phenyl-2-buten-1-ol (Z)
1-dimethylamino-5-methyl-3-phenyl-2-hexen-4-ol (Z)
1-methylamino-3-phenyl-3-phenylthio-2-propene (Z)
1-cyclohexyl-4-dimethylamino-2-phenyl-2-buten-1-ol (Z)
4-dimethylamino-2-phenyl-1-(2-pyridyl)-2-buten-1-ol (Z)
4-dimethylamino-1-(4-fluorophenyl)-2-buten-1-ol (Z)
1-(2-chloro-6-fluorophenyl)-4-dimethylamino-2-phenyl-2-buten-1-ol (Z).

2-Propeneamines with antidepressant properties are known from Belgian Pat. No. 781105; however, none of the products disclosed contains in its molecule a radical Y such as defined in the present invention and nothing in the prior art would prompt the person skilled in the art to introduce such a radical.

For medicinal use, new products of general formula (I) can be employed as such or, where appropriate, in the form of pharmaceutically acceptable salts, that is to say those which are non toxic in the dosages employed.

As examples of pharmaceutically acceptable salts mention can be made of addition salts with inorganic acids (such as hydrochlorides, sulphates, nitrates or phosphates), or organic acids (such as acetates, propionates, succinates, benzoates, fumarates, maleates, methanesulphonates, isethionates, theophyllineacetates, salicylates, phenolphthaleinates, methylenebis-β-oxynaphthoates), or substituted derivatives of these compounds.

The following Examples illustrate the invention. In some examples, the products are purified by "flash chromatography"; this refers to a purification method in which a short chromatography column is employed, operating at an intermediate pressure (50 kPa), using a silica of particle size 40–63 μm, as described by W. C. Still, M. Kahn and A. Mitra, *J. Org. Chem.*, 43, 2923, (1978).

In the NMR spectra which are given, the lower case letters have the following meanings: s=singlet, d=doublet, t=triplet, m=multiplet.

EXAMPLE 1

A 1.5M solution (83 cc) of n-butyllithium in hexane is added, at a temperature in the region of −75° C., to a solution of acetophenone 2,4,6-triisopropylbenzenesulphonylhydrazone (24 g) in 1,2-dimethoxyethane (1000 cc) kept under a nitrogen atmosphere. N,N-dimethylmethyleneammonium iodide (11.1 g) is added to the orange solution obtained; the suspension obtained is stirred vigorously for 20 minutes at a temperature in the region of −50° C.; a 1.5M solution (41.5 cc) of n-butyllithium in hexane is then added at a temperature in the region of −75° C. The reaction mixture is heated slowly up to a temperature in the region of 0° C. Starting from −30° C., a gas release is noted which drops almost to zero when the temperature is in the region of 0° C. The reaction mixture is then cooled to a temperature in the region of −30° C. Benzaldehyde (7.7 g) dissolved in 1,2-dimethoxyethane (200 cc) is then added to it and stirring is continued for 2 hours at a temperature in the region of 20° C. Distilled water (250 cc), concentrated hydrochloric acid (50 cc) and ethyl ether (300 cc) are then added in succession. The aqueous phase is separated; the organic phase is extracted with a 1N aqueous solution of hydrochloric acid (125 cc). The aqueous phases are combined, made alkaline with a 10N aqueous solution of sodium hydroxide to a pH in the region of 11 and are then extracted with ethyl acetate (3×200 cc). The organic phases are combined, dried over magnesium sulphate, filtered and then concentrated to dryness under reduced pressure (2.7 kPa) at 40° C.; the residue obtained is dissolved in a mixture of ethyl ether (140 cc) and ethanol (70 cc); a 3.5N solution (20 cc) of hydrochloric acid gas in ethyl ether is added to the solution obtained. The solid formed is separated by filtration and then recrystallised from acetonitrile. 4-Dimethylamino-1,2-diphenyl-2-buten-1-ol (Z) hydrochloride (10 g) is thus obtained in the form of a white powder melting at 178° C.

Acetophenone 2,4,6-triisopropylbenzenesulphonylhydrazone can be prepared by the method described by M. F. Lipton and R. H. Shapiro, *J. Org. Chem.*, 43, 1409, (1978).

EXAMPLE 2

By using a method similar to that described in Example 1, but starting from acetophenone 2,4,6-triisopropylbenzenesulphonylhydrazone (36.1 g), N,N-dimethylmethyleneammonium iodide (18.5 g) and cyclohexanecarboxaldehyde (11.2 g), 1-cyclohexyl-4-dimethylamino-2-phenyl-2-buten-1-ol (Z) hydrochloride (7.5 g) is obtained, after recrystallisation from acetonitrile, in the form of a white powder melting at 222° C.

EXAMPLE 3

By using a method similar to that described in Example 1, but starting from acetophenone 2,4,6-triisopropylbenzenesulphonylhydrazone (12 g), N,N-dimethylmethyleneammonium iodide (6.1 g) and 4-chlorobenzaldehyde (4.7 g), 1-(4-chlorophenyl)-4-dimethylamino-2-phenyl-2-buten-1-ol (Z) hydrochloride (3 g) is obtained, after recrystallisation from acetone, in the form of a white powder melting at 170° C.

EXAMPLE 4

By using a method similar to that described in Example 1, but starting from acetone 2,4,6-triisopropyl benzenesulphonylhydrazone (12 g), N,N-dimethylmethyleneammonium iodide (6.1 g) and acetophenone (4 g), 4-dimethylamino-1,2-diphenyl-1-methyl-2-buten-1-ol (Z) hydrochloride (2.5 g) is obtained, after recrystallisation from acetone, in the form of a white powder melting at 160° C.

EXAMPLE 5

By using a method similar to that described in Example 1, but starting from acetophenone 2,4,6-triisopropylbenzenesulphonylhydrazone (12 g), N,N-dimethylmethyleneammonium iodide (6.1 g) and 4-bromobenzaldehyde (6.1 g), 1-(4-bromophenyl)-4-dimethylamino-2-phenyl-2-buten-1-ol (Z) hydrochloride (2.1 g) is obtained, after recrystallisation from acetonitrile, in the form of a white powder melting at 163° C.

EXAMPLE 6

By using a method similar to that described in Example 1, but starting from acetophenone 2,4,6-triisopropylbenzenesulphonylhydrazone (12 g), N,N-dimethylmethyleneammonium iodide (6.1 g) and phenylacetaldehyde (3.9 g), 5-dimethylamino-1,3-diphenyl-3-penten-2-ol (Z) hydrochloride (2.3 g) is obtained, after recrystallisation from ethanol, in the form of a white powder melting at 220° C.

EXAMPLE 7

By using a method similar to that described in Example 1, but starting from acetophenone 2,4,6-triisopropylbenzenesulphonylhydrazone (12 g), N,N-dimethylmethyleneammonium iodide (6.1 g) and 3-trifluoromethylbenzaldehyde (5.7 g), 4-dimethylamino-2-phenyl-1-(3-trifluoromethylphenyl)-2-buten-1-ol (Z) hydrochloride (2.1 g) is obtained, after recrystallisation from acetone, in the form of white crystals melting at 180° C.

EXAMPLE 8

By using a method similar to that described in Example 1, but starting from 4-methylacetophenone 2,4,6-triisopropylbenzenesulphonylhydrazone (12.1 g), N,N-dimethylmethyleneammonium iodide (6.1 g) and benzaldehyde (3.5 g), 4-dimethylamino-2-(4-methylphenyl)-1-phenyl-2-buten-1-ol (Z) hydrochloride (2.3 g) is obtained, after recrystallisation from ethanol, in the form of white crystals melting at 185° C.

4-Methylacetophenone 2,4,6-triisopropylbenzenesulphonylhydrazone can be prepared as follows: 4-methylacetophenone (15.4 g) is added to a solution of 2,4,6-triisopropylbenzenesulphonylhydrazine (29.8 g) in methanol (60 cc) containing a 3N solution (37 cc) of hydrochloric acid gas in ethyl ether. The reaction mixture is kept at a temperature in the region of 5° C. for 18 hours, and is then filtered. The crystals obtained are added to a mixture of methylene chloride (300 cc) and a saturated aqueous solution of sodium bicarbonate. The organic phase is separated, dried over magnesium sulphate, filtered and then concentrated to dryness under reduced pressure (2.7 kPa) at 40° C. 4-Methylacetophenone 2,4,6-triisopropylbenzenesulphonylhydrazone (21 g) is obtained, after recrystallisation from ethanol, in the form of white crystals melting at 202° C.

EXAMPLE 9

A 1.5M solution (134 cc) of n-butyllithium in hexane is added at a temperature in the region of −75° C. to a solution of acetophenone 2,4,6-triisopropylbenzenesulphonylhydrazone (36.1 g) in 1,2,-dimethoxyethane (1000 cc) kept under a nitrogen atmosphere. N,N-Dimethylmethyleneammonium iodide (18.5 g) is added to the orange solution obtained; the suspension obtained is stirred vigorously for 20 minutes at a temperature in the region of −50° C. A 1.5M solution (67 cc) of n-butyllithium in hexane is then added at a temperature in the region of −75° C., and the temperature is then allowed to rise slowly to approximately 0° C.

The reaction mixture is then cooled to a temperature in the region of −30° C.; 3-pyridinecarboxaldehyde (10.7 g) dissolved in 1,2-dimethoxyethane (50 cc) is then added and left stirred for 2 hours at a temperature in the region of 20° C. A mixture of ethyl ether (500 cc), an aqueous solution of concentrated hydrochloric acid (100 cc) and distilled water (400 cc) is added. The aqueous phase is separated; the organic phase is extracted with a 1N aqueous solution of hydrochloric acid (50 cc). The aqueous phases are combined, made alkaline to a pH in the region of 11 with a 10N aqueous solution of sodium hydroxide and extracted with ethyl acetate (3×100 cc). The organic phases are combined, dried over magnesium sulphate, filtered and concentrated to dryness under reduced pressure (2.7 kPa) at 40° C. The residue obtained is dissolved in ethanol (100 cc). Oxalic acid (7.7 g) is added to the solution obtained; the crystals which appear are separated off by filtration. After recrystallisation from methanol, 4-dimethylamino-2-phenyl-1-(3-pyridyl)-2-buten-1-ol (Z) sesquioxalate (14.8 g) is obtained in the form of a white powder melting at 195° C.

EXAMPLE 10

By using a method similar to that described in Example 9, but starting from acetophenone 2,4,6-triisopropylbenzenesulphonylhydrazone (12 g), N,N-dimethylmethyleneammonium iodide (6.2 g) and 2-pyridylcarboxaldehyde (3.6 g), 4-dimethylamino-2-phenyl-1-(2-pyridyl)-2-buten-1-ol (Z) sesquioxalate (4.4 g) is obtained, after recrystallisation from ethanol, in the form of white crystals melting at 152° C.

EXAMPLE 11

By using a method similar to that described in Example 9, but starting from acetophenone 2,4,6-triisopropylbenzenesulphonylhydrazone (12 g), N,N-dimethylmethyleneammonium iodide (6.1 g) and 4-pyridinecarboxaldehyde (3.6 g), 4-dimethylamino-2-phenyl-1-(4-pyridyl)-2-buten-1-ol (Z) oxalate (2.5 g) (2.5 moles of oxalic acid per mole of product) is obtained, after recrystallisation from acetone, in the form of yellow crystals melting at 158° C.

EXAMPLE 12

By using a method similar to that described in Example 9, but starting from acetophenone 2,4,6-triisopropylbenzenesulphonylhydrazone (12 g), N,N-dimethylmethyleneammonium iodide (6.1 g) and 4-methoxybenzaldehyde (4.5 g), 4-dimethylamino-1-(4-methoxyphenyl)-2-phenyl-2-buten-1-ol (Z) acid oxalate (3.5 g) is obtained, after recrystallisation from acetone, in the form of white crystals melting at 110° C.

EXAMPLE 13

By using a method similar to that described in Example 9, but starting from 4-methoxyacetophenone 2,4,6-triisopropylbenzenesulphonylhydrazone (12.9 g), N,N-dimethylmethyleneammonium iodide (6.1 g) and benzaldehyde (3.5 g), 4-dimethylamino-2-(4-methoxyphenyl)-1-phenyl-2-buten-1-ol (Z) acid oxalate (1.6 g) is obtained, after recrystallisation from acetone, in the form of white crystals melting at 98° C.

4-Methoxyacetophenone 2,4,6-triisopropylbenzenesulphonylhydrazone can be prepared by a method similar to that described in Example 8 for the preparation of 4-methylacetophenone 2,4,6-triisopropylbenzenesulphonylhydrazone. By starting from 2,4,6-triisopropylbenzenesulphonylhydrazine (29.8 g) and 4-methoxyacetophenone (15 g), 4-methoxyacetophenone 2,4,6-triisopropylbenzenesulphonylhydrazone (28 g) is obtained, after recrystallisation from ethanol, in the form of white crystals melting at 210° C.

EXAMPLE 14

By using a method similar to that described in Example 9, but starting from acetophenone 2,4,6-triisopropylbenzenesulphonylhydrazone (12 g), N,N-dimethylmethyleneammonium iodide (6.1 g) and 4-fluorobenzaldehyde (4.1 g), 4-dimethylamino-1-(4-fluorophenyl)-2-phenyl-2-buten-1-ol (Z) acid oxalate (2 g) is obtained, after recrystallisation from acetone, in the form of white crystals melting at 125° C.

EXAMPLE 15

By using a method similar to that described in Example 9, but starting from acetophenone 2,4,6-triisopropylbenzenesulphonylhydrazone (12 g), N,N-dimethylmethyleneammonium iodide (6.1 g) and 2-chloro-6-fluorobenzaldehyde (5.5 g), 1-(2-chloro-6-fluorophenyl)-4-dimethylamino-2-phenyl-2-buten-1-ol (Z) acid oxalate (2.2 g) is obtained, after recrystallisation from acetone, in the form of white crystals melting at 88° C.

EXAMPLE 16

A solution of ethyl ether (10 cc) and of a 1.5N solution (6.4 cc) of n-butyllithium in hexane is added to a solution of 3-bromo-3-phenyl-1-dimethylamino-2-propene (Z) (2.3 g) in ethyl ether (40 cc) kept under a nitrogen atmosphere at a temperature in the region of −78° C. and is left stirred for 15 minutes. A solution of benzaldehyde (1 cc) in 1,2-dimethoxyethane (10 cc) is added to the brown solution obtained and stirring is continued at a temperature in the region of −10° C. for 2 hours. The reaction mixture is then poured into distilled water (50 cc), adjusted to pH 2 with an aqueous solution of concentrated hydrochloric acid. The aqueous phase is separated, made alkaline to pH 10 by addition of a 10N aqueous solution of sodium hydroxide and then extracted with ethyl ether (2×200 cc). The organic phases are dried over sodium sulphate, filtered and then concentrated to dryness under reduced pressure (2.7 kPa) at 40° C. The light yellow oil obtained is purified by "flash" chromatography [eluent: ethyl acetate/methanol (50/50 by volume)]. After fractions 38 to 53 have been evaporated to dryness under reduced pressure (2.7 kPa) at 40° C., a residue obtained which is dissolved in ethanol (1 cc) and ethyl ether (0.3 cc). A 3.5N solution (0.7 cc) of hydrochloric acid gas in ethyl ether is added to the solution obtained. A solid precipitates; it is separated off by filtration. In this way 4-dimethylamino-1,2-diphenyl-2-buten-1-ol (Z) hydrochloride (0.3 g) is obtained in the form of a white powder melting at 172°–174° C.

3-Bromo-3-phenyl-1-dimethylamino-2-propene (Z) can be prepared as follows: a solution of phosphorus oxybromide (54.2 g) in methylene chloride (45 cc) is added at a temperature in the region of 10° C. to a solution of dimethylaminoacrylophenone (33.1 g) in methylene chloride (120 cc) and is left stirred for 45 minutes at a temperature in the region of 10° C. and then 30 minutes at ambient temperatures. Methanol (150 cc) is then added at a temperature in the region of 0° C. After 10 minutes, sodium cyanoborohydride (7.15 g) is added and stirring is continued for 3 hours at ambient temperature. The reaction mixture is evaporated to dryness under reduced pressure (2.7 kPa) at 30° C.; an orange oil is thus obtained, which is taken up in methylene chloride; the solution is filtered and then poured into iced water (200 cc). After being made alkaline to pH 10 by adding a 10N aqueous solution of sodium hydroxide, the organic phase is separated, dried over sodium sulphate, filtered and evaporated to dryness under reduced pressure (2.7 kPa) at 30° C. A red oil is obtained, which is dissolved in a mixture of ethanol (50 cc) and ethyl ether (75 cc); a 3.5N solution (60 cc) of hydrochloric acid gas in ethyl ether is added to the solution obtained. The solid formed is separated off by filtration and then recrystallised from acetone (720 cc). 3-Bromo-3-phenyl-1- dimethylamino-2-propene (Z) (15.3 g) is thus obtained in the form of a white powder melting at 174° C.

Dimethylaminoacrylophenone can be prepared by the method described by H. Meerwein, W. Florian, N. Schor, G. Stopp, *Ann. Chem.* 641, 1, (1961).

EXAMPLE 17

By using a method similar to that described in Example 16, but starting from 3-bromo-3-(4-chlorophenyl)-1-dimethylamino-2-propene (Z) (21.4 g), a 1.5N solution (56 cc) of n-butyllithium in hexane, and benzaldehyde (9.8 cc), and after purification by "flash" chromatography [eluent: methylene chloride/methanol (95/5 by volume)] and concentrating fractions 30 to 54 to dryness under reduced pressure (2.7 kPa) at 40° C., a residue is obtained which is dissolved in ethanol (10 cc). A 3.5N solution (5 cc) of hydrochloric acid gas in diethyl ether is added to the solution obtained. The solid which precipitates is separated off by filtration and then recrystallised from ethanol. 2-(4-Chlorophenyl)-4-dimethylamino-1-phenyl-2-buten-1-ol (Z) hydrochloride (3 g) is thus obtained in the form of a white powder melting at 172° C.

3-Bromo-3-(4-chlorophenyl)-1-dimethylamino-2-propene (Z) can be prepared by a method similar to that described in Example 16, but starting from 1-(4-chlorophenyl)-3-dimethylamino-2-buten-1-one, phosphorus oxybromide (61.3 g) and sodium cyanoborohydride (8.10 g). Evaporation to dryness under reduced pressure (2.7 kPa) at 30° C. of the reaction mixture produces a yellow solid which is taken up on chloroform. The solution is filtered and the filtrate is evaporated under reduced pressure (2.7 kPa) at 30° C. The solid obtained is washed with a methanol/ethyl ether mixture (75/25 by volume). In this way 3-bromo-3-(4-chlorophenyl)-1-dimethylamino-2-propene (Z) hydrobromide (45.9 g) is obtained in the form of a white solid melting at 174° C.

1-(4-Chlorophenyl)-3-dimethylamino-2-buten-1-one can be prepared by the method described by Yang-I-Lin and S. A. Lang, Jr., *J. Org. Chem.*, 45, 4857, (1980).

EXAMPLE 18

By using a method similar to that described in Example 16, but starting from 3-bromo-3-(4-chlorophenyl)-1-dimethylamino-2-propene (Z) (10 g), a 1.5N solution (26 cc) of n-butyllithium in hexane and 3-pyridinecarboxaldehyde (4.20 g), an oil is obtained, which is purified by "flash" chromatography [eluent: methylene chloride/methanol (90/10 by volume)]. After fractions 19 to 50 have been evaporated to dryness under reduced pressure (2.7 kPa) at 40° C., a residue is obtained which is dissolved in ethanol (25 cc). A 1.7M ethanolic solution (13 cc) of oxalic acid is added to the solution obtained; the precipitate which is formed is separated off by filtration and then recrystallised from methanol (36 cc) and distilled water (4 cc). In this way 2-(4-chlorophenyl)-4-dimethylamino-1-(3-pyridyl)-2-buten-1-ol (Z) sesquioxalate (3.5 g) is obtained in the form of white crystals melting at 187° C.

EXAMPLE 19

By using a method similar to that described in Example 16, but starting from 3-bromo-3-(4-fluorophenyl)-1-dimethylaminopropene (Z) (20 g), a 1.5N solution (57 cc) of n-butyllithium in hexane, and benzaldehyde (10 cc), an oil is obtained which is purified by "flesh" chromatography [eluent: methylene chloride/methanol (90/10 by volume)]. After fractions 36 to 79 have been evaporated to dryness under reduced pressure (2.7 kPa) at 40° C., a residue is obtained which is dissolved in acetonitrile (20 cc) and ethyl ether (60 cc). A 3N solution (5.6 cc) of hydrochloric acid gas in ethyl ether is added to the solution obtained. The precipitate which is formed is separated off by filtration and then recrystallised from isopropanol (15 cc). In this way 4-dimethylamino-2-(4-fluorophenyl)-1-phenyl-2-buten-1-ol (Z) hydrochloride (2 g) is obtained in the form of white crystals melting at 141° C.

3-Bromo-3-(4-fluorophenyl)-1-dimethylamino-2-propene (Z) can be prepared by a method similar to that described in Example 16, but starting from 1-(4-fluorophenyl)-3-dimethylamino-2-buten-1-one (26.5 g), phosphorus oxybromide (39.15 g) and sodium cyanoborohydride (5.15 g). Evaporation of the reaction mixture to dryness under reduced pressure (2.7 kPa) at 30° C. produces a yellow solid which is taken up in chloroform. After filtration, the chloroform phase is evaporated under reduced pressure (2.7 kPa) at 30° C. to give a solid which is crystallised from methanol (50 cc) and ethyl ether (25 cc). In this way 3-bromo-3-(4-fluorophenyl)-1-dimethylamino-2-propene (Z) hydrobromide (30 g) is obtained in the form of a white solid melting at approximately 156° C.

1-(4-Fluorophenyl)-3-dimethylamino-2-buten-1-one can be prepared by the method described by J. D. Albright et al., U.S. Pat. No. 4,209,621.

EXAMPLE 20

By using a method similar to that described in Example 16, but starting from 3-bromo-3-phenyl-1-(N-piperidino)-2-propene (Z) (13.6 g), a 1.5N solution (36 cc) of n-butyllithium in hexane, and benzaldehyde (6.5 cc), and after a 1N aqueous solution (50 cc) of hydrochloric acid has been added to the reaction mixture at 0° C., a white precipitate is obtained. After the precipitate has been separated off by filtration and washed with ethyl ether, the solid obtained is taken up in methylene chloride. The organic phase is dried over sodium sulphate, filtered and evaporated to dryness under reduced pressure (2.7 kPa) at 30° C., to give a residue which is recrystallised from isopropanol (80 cc). In this way 1,2-diphenyl-4-(N-piperidino)-2-buten-1-ol (Z) hydrochloride (2.7 g) is obtained in the form of white crystals melting at 195°-196° C.

3-Bromo-3-phenyl-1-(N-piperidino)-2-propene (Z) can be prepared by a method similar to that described in Example 16, but starting from 3-N-piperidinoacrylophenone (29.1 g), phosphorus oxybromide (38.8 g) and sodium cyanoborohydride (5.1 g). Evaporation of the reaction mixture to dryness under reduced pressure (2.7 kPa) at 30° C. produces a yellow solid which is taken up in chloroform. After filtration, the chloroform phase is concentrated under reduced pressure (2.7 kPa) at 30° C. to give a yellow solid which is crystallised from isopropanol. In this way 3-bromo-3-phenyl-1(N-piperidino)-2-propene (Z) hydrobromide (26.5 g) is obtained in the form of a white solid melting at 204°-205° C.

3-N-Piperidinoacrylophenone can be prepared by a method similar to that described by E. Benary, *Ber*, 63, 1573 (1930).

EXAMPLE 21

By using a method similar to that described in Example 16, but starting from 3-bromo-3-(4-bromophenyl)-1-dimethylamino-2-propene (Z) (21 g), a 1.5N solution (48 cc) of n-butyllithium in hexane, and benzaldehyde (8.5 cc), an oil is obtained which is purified by "flash" chromatography [eluent: dichloromethane/methanol (93/7 by volume)]. After fractions 25 to 39 have been evaporated to dryness under reduced pressure (2.7 kPa) at 40° C., a residue is obtained, which is dissolved in acetonitrile (40 cc). A 3N solution (9.7 cc) of hydrochloric acid gas in ethyl ether is added to the solution obtained; the solid which is formed is separated off by filtration and then recrystallised from acetonitrile (100 cc). In this way 2-(4-bromophenyl)-4-dimethylamino-1-phenyl-2-buten-1-ol (Z) hydrochloride (5.2 g) is obtained in the form of a white solid melting at 178° C.

3-Bromo-3-(4-bromophenyl)-1-dimethylamino-2-propene (Z) can be prepared by a method similar to that described in Example 16, but starting from 1-(4-bromophenyl)-3-dimethylamino-2-propen-1-one (38 g), phosphorus oxybromide (42.9 g) and sodium cyanoborohydride (5.68 g). Evaporation of the reaction mixture to dryness under reduced pressure (2.7 kPa) at 30° C. produces a yellow solid which is crystallised from methanol. In this way, 3-bromo-3-(4-bromophenyl)-1-dimethylamino-2-propene (Z) hydrobromide (28 g) is obtained in the form of a white solid melting at 180° C.

1-(4-Bromophenyl)-3-dimethylamino-2-propen-1-one can be prepared by a method similar to that described by Yang-I-Lin and S. A. Lang Jr., *J. Org. Chem.*, 45, 4857, (1980).

EXAMPLE 22

A 1.5M solution (29 cc) of n-butyllithium in hexane is added to a solution of β-dimethylaminopropiophenone 2,4,6-triisopropylbenzenesulphonylhydrazone (9.15 g) in 1,2-dimethoxyethane (100 cc) kept under a nitrogen atmosphere at a temperature in the region of −75° C. The orange solution obtained is then stirred for 15 minutes at a temperature in the region of 0° C., and then cooled to a temperature in the region of −40° C. Benzaldehyde (2.2 cc) is then added, and then the reaction mixture is stirred for 1 hour at a temperature in the region of 20° C. A 1N aqueous solution (100 cc) of hydrochloric acid is then added with stirring, followed by ethyl ether (100 cc). The aqueous phase is separated; the organic phase is extracted with a 0.1N aqueous solution (25 cc) of hydrochloric acid. The aqueous phases are combined, washed with ether (2×50 cc) and then made alkaline to a pH in the region of 10 with sodium hydroxide solution, and then extracted with ethyl acetate (3×50 cc). The organic phases are combined, dried over magnesium sulphate, filtered and then concentrated to dryness under reduced pressure (2.7 kPa) at 40° C. In this way 4-dimethylamino-1,2-diphenyl-2-buten-1-ol (Z) (5.2 g) is obtained in the form of white crystals melting at 75° C.

β-Dimethylaminopropiophenone 2,4,6-triisopropylbenzenesulphonylhydrazone can be prepared as follows: β-dimethylaminopropiophenone hydrochloride (77.3 g), followed by distilled water (33 cc) are added to a suspension of 2,4,6-triisopropylbenzenesulphonylhydrazine in a mixture of methanol (130 cc) and a 3N solution (130 cc) of hydrochloric acid gas in ethyl ether, and the reaction mixture is stirred at a temperature in the region of 20° C. for 20 hours. The reaction mixture is cooled to a temperature in the region of +5° C.; the crystals formed are separated off by filtration and then added to a mixture of methylene chloride (550 cc), a 4N aqueous solution (110 cc) of sodium hydroxide and distilled water (275 cc), and the mixture is stirred vigorously. The organic phase is then separated; the aqueous phase is extracted with methylene chloride (3–150 cc). The organic phases are combined, dried over magnesium sulphate, filtered and then concentrated to dryness under reduced pressure (2.7 kPa) at 40° C. The residue obtained is crystallised from isopropanol; in this way β-dimethylaminopropiophenone 2,4,6-triisopropylbenzenesulphonylhydrazone (79 g) is obtained in the form of a white powder melting at 164° C.

EXAMPLE 23

By using a method similar to that described in Example 22, but starting from β-diethylaminopropiophenone 2,4,6-triisopropylbenzenesulphonylhydrazone (30 g) and benzaldehyde (6.9 cc), 4-diethylamino-1,2-diphenyl-2-buten-1-ol (Z) hydrochloride (3.2 g) is obtained, after recrystallisation from acetone, in the form of white crystals melting at 140° C.

β-Diethylaminopropiophenone 2,4,6-triisopropylbenzenesulphonylhydrazone can be prepared by a method similar to that described in Example 22 for the preparation of β-diethylaminopropiophenone 2,4,6-triisopropylbenzenesulphonylhydrazone but starting from 2,4,6-triisopropylbenzenesulphonylhydrazine (51.8 g) and β-diethylaminopropiophenone hydrochloride (64.4 g). In this way β-diethylaminopropiophenone 2,4,6-triisopropylbenzenesulphonylhydrazone (53.6 g) is obtained in the form of cream crystals melting at 134° C.

β-Diethylaminopropiophenone hydrochloride can be prepared by the method described by C. E. Maxwell, *Org. Synth.* Coll. Vol. III, John Wiley & Sons, London (1955) page 305.

EXAMPLE 24

By using a method similar to that described in Example 22, but starting from β-(1-pyrrolidinyl)propiophenone 2,4,6-triisopropylbenzenesulphonylhydrazone (20 g), and benzaldehyde (4.6 cc), 1,2-diphenyl-4-(1-pyrrolidinyl)-2-buten-1-ol (Z) hydrochloride (9.9 g) is obtained, after recrystallisation from a mixture of 2-propanol and isopropyl ether (40/60 by volume), in the form of white crystals melting at 106° C.

β-(1-Pyrrolidinyl)propiophenone 2,4,6-triisopropylbenzenesulphonylhydrazone can be prepared by a method similar to that described in Example 22 for the preparation of β-dimethylaminopropiophenone 2,4,6-triisopropylbenzenesulphonylhydrazone, but starting from 2,4,6-triisopropylbenzenesulphonylhydrazine (17.9 g) and β-(1-pyrrolidinyl)propiophenone hydrochloride (14.4 g). In this way β-(1-pyrrolidinyl)propiophenone 2,4,6-triisopropylbenzenesulphonylhydrazone (20 g) is obtained in the form of white crystals melting at 142° C.

β-(1-Pyrrolidinyl)propiophenone hydrochloride can be prepared by a method similar to that described by C. E. Maxwell, *Org. Synth.*, coll. Vol VII, John Wiley & Sons, London (1955) page 305, but starting from pyrrolidine hydrochloride (58.8 g) acetophenone (60.1 g) and polyoxymethylene (22.5 g). In this way β-(1-pyrrolidinyl)propiophenone hydrochloride (66 g) is obtained in the form of white crystals melting at 164° C.

EXAMPLE 25

By proceeding as in Example 22 but starting from β-dimethylaminopropiophenone 2,4,6-triisopropylbenzenesulphonylhydrazone (18.9 g), a 1.5M solution (61 cc) of n-butyllithium and 3-chlorobenzaldehyde (6.4 g)

in 1,2-dimethoxyethane (190 cc) and after recrystallising from isopropanol (125 cc), 1-(3-chloropheny)-4-dimethylamino-2-phenyl-2-buten-1-ol (Z) hydrochloride (8.9 g) is obtained, melting at 185° C.

EXAMPLE 26

By proceeding as in Example 22 but starting from β-dimethylaminopropiophenone 2,4,6-triisopropylbenzenesulphonylhydrazone (15 g), a 1.5M solution (48 cc) of n-butyllithium in hexane, and 3-fluorobenzaldehyde (4.5 g), in 1,2-dimethoxyethane (150 cc), and after recrystallising from a mixture (215 cc) of acetone and isopropanol (93/7 by volume), 1-(3-fluorophenyl)-4-dimethylamino-2-phenyl-2-buten-1-ol (Z) hydrochloride (5.3 g), melting at 165° C., is obtained.

EXAMPLE 27

By proceeding as in Example 22 but starting from β-dimethylaminopropiophenone 2,4,6-triisopropylbenzenesulphonylhydrazone (20 g), a 1.5M solution (64 cc) of n-butyllithium in hexane, and 2-chlorobenzaldehyde (6.8 g), in 1,2-dimethoxyethane (200 cc), and after recrystallising the crude product in the base form from a mixture (62 cc) of isopropyl ether and petroleum ether (50/50 by volume), 1-(2-chlorophenyl)-4-dimethylamino-2-phenyl-2-buten-1-ol (Z) (5.2 g), melting at 90° C. is obtained.

EXAMPLE 28

By proceeding as in Example 22 but starting from β-dimethylaminopropiophenone 2,4,6-triisopropylbenzenesulphonylhydrazone (20 g), a 1.5M solution (64 cc) of n-butyllithium in hexane, and 3-methoxybenzaldehyde (6.5 g) in 1,2-dimethoxyethane (200 cc), and after recrystallising the crude product in the base form from acetone (200 cc), 1-(3-methoxyphenyl)-4-dimethylamino-2-phenyl-2-buten-1-ol (Z) (4.7 g), melting at 160° C., is obtained.

EXAMPLE 29

By proceeding as in Example 22 but starting from β-dimethylaminopropiophenone 2,4,6-triisopropylbenzenesulphonylhydrazone (20 g), a 1.5M solution (64 cc) of n-butyllithium in hexane and 2,3-dimethoxybenzaldehyde (8 g), in 1,2-dimethoxyethane (200 cc), and after recrystallising the crude product in the base form from isopropyl ether (100 cc), 1-(2,3-dimethoxyphenyl)-4-dimethylamino-2-phenyl-2-buten-1-ol (Z) (6.7 g), melting at 105° C., is obtained.

EXAMPLE 30

Sodium borohydride (10.3 g) is added over approximately 30 minutes at a temperature in the region of 5° C. to a solution of 2,3-diphenyl-5-methylamino-2,5-dihydrofuran (9.7 g) in methanol (90 cc) and distilled water (10 cc). The reaction mixture is then stirred for 18 hours at a temperature in the region of 20° C., and then concentrated to dryness under reduced pressure (2.7 kPa) at 40° C. The residue obtained is triturated with methylene chloride (100 cc); the suspension obtained is filtered and the filtrate is concentrated to dryness under reduced pressure (2.7 kPa) at 40° C. The residue is purified by chromatography on silica gel (400 g) in a 4 cm diameter column [eluent: methanol/aqueous ammonia (98/2 by volume)]. Elution is first carried out with solvent (400 cc); the corresponding eluate is discarded; elution then continues with solvent (600 cc); the corresponding eluate is concentrated to dryness under reduced pressure (2.7 kPa) at 40° C. The residue obtained is recrystallised from a mixture of hexane (70 cc) and isopropanol (10 cc). In this way 1,2-diphenyl-4-methylamino-2-buten-1-ol (Z) (3.8 g) is obtained in the form of white crystals melting at 90° C.

2,3-Diphenyl-5-methylamino-2,5-dihydrofuran can be prepared as follows: benzoin (29.7 g) dissolved in tetrahydrofuran (400 cc) is added to a suspension of sodium hydride (3.4 g) in tetrahydrofuran (50 cc) kept under a nitrogen atmosphere at a temperature in the region of 0° C., and the reaction mixture is stirred for 30 minutes while the temperature is allowed to return to 20° C. Diethyl 2-methyliminoethylphosphonate (27 g) in tetrahydrofuran (270 cc) is then added. The reaction mixture is then heated to reflux for 1 hour and then cooled to a temperature in the region of 20° C. Water (1 liter) is then added and the mixture is extracted twice with ethyl acetate (200 cc in total). The organic phase is washed with water (2×100 cc) and then dried over magnesium sulphate, filtered and then evaporated to dryness under reduced pressure (2.7 kPa) at 40° C. The residue is washed with ethyl ether (100 cc) and then filtered. The filtrate is evaporated to dryness under reduced pressure (2.7 kPa) at 40° C. to give an oil which is purified by "flash" chromatography [eluent: ethyl acetate]. After fractions 8 to 19 have been evaporated to dryness under reduced pressure (2.7 kPa) at 40° C., an orange oil is obtained which is dissolved in a mixture (20 cc) of ethyl acetate and ethyl ether (50/50 by volume). A 5.7N solution (3.9 cc) of hydrochloric acid gas in ethyl ether is added to the solution. The solid obtained is separated off by filtration and then recrystallised from isopropanol (120 cc). In this way 2,3-diphenyl-5-methylamino-2,5-dihydrofuran hydrochloride (2.8 g) is obtained in the form of a white solid melting at 190° C.

Diethyl 2-methyliminoethylphosphonate can be prepared as follows: a 33% solution (16.5 cc) of methylamine is added to a solution of diethylphosphonoacetaldehyde (32.4 g) in methanol (100 cc). The reaction mixture is stirred for 3 hours at a temperature in the region of 20° C., and is then concentrated to dryness under reduced pressure (2.7 kPa) at 40° C. The residue is dissolved in the minimum quantity of ethyl ether; the solution obtained is dried over potassium carbonate, filtered and then concentrated to one third of the original volume under reduced pressure (2.7 kPa) at 20° C. The crystals obtained are separated off by filtration and then dried at a temperature in the region of 20° C. In this way diethyl 2-methyliminoethylphosphonate (18.4 g) is obtained in the form of a yellow powder melting at 66° C.

Diethylphosphonoacetaldehyde can be prepared by the method described by N. D. Dawson and A. Burger, *J. Am. Chem. Soc.*, 74, 5312, (1952).

EXAMPLE 31

By using a method similar to that described in Example 30, but starting from 2,3-diphenyl-5-ethylamino-2,5-dihydrofuran (25 g) and sodium borohydride (25 g), and after purification by chromatography on silica gel (eluent: methanol) followed by recrystallisation from isopropyl ether, 1,2-diphenyl-4-ethylamino-2-buten-1-ol (Z) (8.4 g) is obtained in the form of of a white powder melting at 82° C.

2,3-Diphenyl-5-ethylamino-2,5-dihydrofuran can be prepared by a method similar to that described in Example 30, but starting from diethyl 2-ethyliminoethylphosphonate (63 g), benzoin (64 g) and sodium hydride (6.55 g). An oil is obtained, which is purified by chromatography on silica gel [eluent: ethyl acetate/cyclohexane (50/50 by volume)]. In this way 2,3-diphenyl-5-ethylamino-2,5-dihydrofuran (25g) is obtained in the form of an orange-yellow oil [$R_f$=0.4; chromatography on silica gel; eluent: ethyl acetate/cyclohexane (50/50 by volume)].

Diethyl 2-ethyliminoethylphosphonate can be prepared by a method similar to that described in Example 30, but starting from diethylphosphonoacetaldehyde (60 g) and ethylamine (15 g). After the reaction mixture has been concentrated to dryness under reduced pressure (2.7 kPa) at 40° C., diethyl 2-ethyliminoethylphosphonate (63.8 g) is obtained in the form of a yellow oil [$R_f$=0.47; chromatography on silica gel; eluent: ethyl acetate/methanol (92.5/7.5 by volume)].

EXAMPLE 32

By using a method similar to that described in Example 30, but starting from 2,3-diphenyl-5-(2-propylamino)-2,5-dihydrofuran (33.3 g) and sodium borohydride (31.6 g), 1,2-diphenyl-4-(2-propylamino)-2-buten-1-ol (Z) hydrochloride (9.4 g) is obtained, in the form of white crystals melting at 188° C., after conversion to the hydrochloride in ethyl ether and recrystallisation of this hydrochloride from ethanol.

2,3-Diphenyl-5-(2-propylamino)-2,5-dihydrofuran can be prepared by a method similar to that described in Example 30, but starting from diethyl 2-(2-propylamino)ethylphosphonate (66 g), benzoin (63.3 g) and sodium hydride (12.9 g). In this way 2,3-diphenyl-5-(2-propylamino)-2,5-dihydrofuran (33.3 g) is obtained in the form of a yellow oil [$R_f$=0.46; thin layer chromatography on silica gel, eluent: ethyl acetate/cyclohexane (50/50 by volume)].

Diethyl 2-(2-propylimino)ethylphosphonate can be prepared by a method similar to that described in Example 30, but starting from diethylphosphonoacetaldehyde (60 g) and isopropylamine (19.7 g). In this way diethyl 2-(2-propylimino)ethylphosphonate (67.9 g) is obtained in the form of a yellow oil [$R_f$=0.53; thin layer chromatography on silica gel, eluent: ethyl acetate/methanol (92.5/7.5 by volume)].

EXAMPLE 33

By using a method similar to that described in Example 30, but starting from 5-butylamino-2,3-diphenyl-2,5-dihydrofuran (29.6 g) and sodium borohydride (26.7 g), and after conversion to the hydrochloride in ethyl ether and recrystallisation of this hydrochloride from acetone, 4-butylamino-1,2-diphenyl-2-buten-1-ol (Z) hydrochloride (4.3 g) is obtained in the form of white crystals melting at 155° C.

5-Butylamino-2,3-diphenyl-2,5-dihydrofuran can be prepared by a method similar to that described in Example 30, but starting from diethyl 2-butyliminoethylphosphonate (64 g), benzoin (57.7 g) and sodium hydride (11.8 g); in this way, 5-butylamino-2,3-diphenyl-2,5-dihydrofuran (29.6 g) is obtained in the form of an orange oil [$R_f$=0.50; thin layer chromatography on silica gel, eluent: ethyl acetate/cyclohexane (50/50 by volume)].

Diethyl 2-butyliminoethylphosphonate can be prepared by a method similar to that described in Example 30 but starting from diethylphosphonoacetaldehyde (54 g) and butylamine (21.9 g). In this way diethyl 2-butyliminoethylphosphonate (66.2 g) is obtained in the form of a yellow oil [$R_f$=0.40; thin layer chromatography on silica gel, eluent: ethyl acetate/methanol (92.5/7.5 by volume)].

EXAMPLE 34

By using a method similar to that described in Example 30, but starting from 5-allylamino-2,3-diphenyl-2,5-dihydrofuran (26.9 g) and sodium borohydride (25 g), a crude product is obtained which is purified by chromatography on silica gel (100 g) in an 8 cm diameter column (eluent: methanol). The yellow oil obtained (6 g) is dissolved in ethyl ether (100 cc).

A 3.5N solution (20 cc) of hydrochloric acid gas in ethyl ether is added to the solution obtained. The crystals which precipitate are separated off by filtration and recrystallised from a mixture of isopropyl ether and acetone (50/50 by volume). In this way 4-allylamino-1,2-diphenyl-2-buten-1-ol (Z) hydrochloride (4.2 g) is obtained in the form of a white powder melting at 113° C.

5-Allylamino-2,3-diphenyl-2,5-dihydrofuran can be prepared by a method similar to that described in Example 30 for the synthesis of 2,3-diphenyl-5-methylamino-2,5-dihydrofuran, but starting from diethyl 2-allyliminoethylphosphonate (32.3 g), benzoin (31.3 g) and sodium hydride (3.2 g). In this way 5-allylamino-2,3-diphenyl-2,5-dihydrofuran (26.9 g) is obtained in the form of a yellow oil [$R_f$=0.5; thin layer chromatography on silica gel, eluent: cyclohexane/ethyl acetate (50/50 by volume)].

Diethyl 2-allyliminoethylphosphonate can be prepared by a method similar to that described in Example 30 for the preparation of diethyl 2-methyliminoethylphosphonate, but starting from diethylphosphonoacetaldehyde (29 g) and allylamine (11.8 cc). Diethyl 2-allyliminoethylphosphonate (32.3 g) is obtained in the form of a yellow oil [$R_f$=0.38; thin layer chromatography on silica gel; eluent: ethyl acetate/methanol (92.5/7.5 by volume)].

EXAMPLE 35

Phosphorus oxychloride (2.5 cc) dissolved in methylene chloride (6 cc) is added dropwise at 0° C. to a solution of 3-dimethylaminoacrylophenone (5 g) in methylene chloride (16 cc). After starting for 15 minutes at 0° C. and then 30 minutes at 20° C., the temperature is again brought down to 0° C. The precipitate formed is dissolved by adding methanol (5 cc). Triethylamine (8 cc) and thiophenol (3.15 cc) dissolved in methylene chloride (10 cc) are added dropwise. After 2 hours 30 minutes' stirring at 20° C., methanol (30 cc) is added followed by sodium cyanoborohydride (1 g) at 0° C. and stirring is continued for 3 hours at 20° C. The mixture is then concentrated under reduced pressure (2.7 kPa) at 40° C. The solid obtained is taken up in chloroform and the solution is filtered. The organic phase is evaporated under reduced pressure (2.7 kPa) at 40° C. The residue obtained is taken up in water and the solution is made alkaline to pH 10 by adding a 35% strength aqueous solution of sodium hydroxide, and then extracted with methylene chloride. The organic phase is dried over sodium sulphate, filtered and then evaporated to dryness under reduced pressure (2.7 kPa) at 40° C. The residue obtained is dissolved in ethyl ether (10 cc). A 3N solution (10 cc) of hydrochloric acid gas in ethyl ether is added to the solution obtained. The precipitate formed is separated off by filtration and then recrystallised from a mixture of ethanol (15 cc) and ethyl ether (20 cc). In this way 1-dimethylamino-3-phenyl-3-phenylthio-2-propene (Z) hydrochloride (3 g) is obtained in the form of white crystals melting at 176° C.

3-Dimethylaminoacrylophenone can be prepared by the method described by H. Meerwein, W. Florian, N. Schon and G. Stopp, *Ann. Chem.* 641, 1, (1961).

EXAMPLE 36

By using a method similar to that described in Example 35, but starting from 3-dimethylaminoacrylophenone (80 g), phosphorus oxychloride (40 cc), thiophenol (50.3 cc) and sodium cyanoborohydride (16 g), and crystallising the (Z)-isomer, a yellow solid is isolated after evaporation of the mother liquors under reduced pressure (2.7 kPa) at 30° C. followed by crystallisation of the residue obtained from a mixture of acetone and ethyl ether (25/75 by volume); the solid is recrystallised from methyl ethyl ketone (230 cc). 1-Dimethylamino-3-phenyl-3-phenylthio-2-propene (E) hydrochloride (14.3 g) is thus obtained in the form of a white solid melting at 146°–147° C.

EXAMPLE 37

By using a method similar to that described in Example 35, but starting from 3-dimethylaminoacrylophenone (5 g), phosphorus oxychloride (2.5 cc), p-chlorothiophenol (4.13 g) and sodium cyanoborohydride (1 g), and after evaporating the reaction mixture under reduced pressure (2.7 kPa) at 40° C., a residue is obtained, which is dissolved in ethanol (50 cc). A 3N solution (12 cc) of hydrochloric acid gas in ethyl ether is added to this solution. The precipitate formed is separated off by filtration and then recrystallised from ethanol (70 cc). In this way 3-(4-chlorophenylthio)-1-dimethylamino-3-phenylthio-2-propene (Z) hydrochloride (3.4 g) is obtained in the form of a white powder melting at 226° C.

EXAMPLE 38

By using a method similar to that described in Example 35, but starting from 3-dimethylaminoacrylophenone (10 g), phosphorus oxychloride (5 cc), 4-mercaptopyridine (6.35 g) and sodium cyanoborohydride (2 g), a chestnut-coloured residue is obtained which is taken up in water (100 cc). The solution is acidified to pH 2 by adding an aqueous solution of concentrated hydrochloric acid and then washed with ethyl ether (2×50 cc). The aqueous phase is adjusted to pH 10 by adding a concentrated aqueous solution of sodium hydroxide and then extracted with methylene chloride. The resultant organic phase is dried over sodium sulphate, filtered and then concentrated to dryness under reduced pressure (2.7 kPa) at 30° C. to give a red residue which is chromatographed on silica gel [eluent: methylene chloride/methanol (95/5 by volume)], 200 cc fractions being collected. Fractions 13 to 25 are concentrated under reduced pressure (2.7 kPa) at 30° C. A residue is obtained which is dissolved in ethanol (15 cc). A 1.2N ethanolic solution (20 cc) of oxalic acid is added to this solution; the solid which precipitates is separated off by filtration and recrystallised from a mixture (110 cc) of acetonitrile and ethanol (20/80 by volume). In this way 1-dimethylamino-3-phenyl-3-(4-pyridylthio)-2-propene (Z) sesquioxalate (3 g) is obtained in the form of white crystals melting at 173° C.

EXAMPLE 39

By using a method similar to that described in Example 35, but starting from 1-(4-chlorophenyl)-3-dimethylamino-2-propen-1-one (10 g), phosphorus oxychloride (4.2 cc), thiophenol (5.2 cc) and sodium cyanoborohydride (1.79 g), an orange residue is obtained which is taken up in water (100 cc). The solution is made alkaline to pH 10 by adding a concentrated aqueous solution of sodium hydroxide and then extracted with methylene chloride. The organic phase is dried over sodium sulphate, filtered, and then evaporated to dryness under reduced pressure (2.7 kPa) at 30° C. The residue obtained is purified by "flash" chromatography [eluent: methylene chloride/methanol (95/5 by volume)]. After fractions 33 to 60 have been evaporated to dryness under reduced pressure (2.7 kPa) at 30° C., a yellow oil (7.8 g) is obtained. This oil is dissolved in acetone (50 cc) and a 1.3M solution (20 cc) of oxalic acid in acetone is added to the solid obtained. The white solid which precipitates is separated off by filtration and recrystallised from ethanol (130 cc). In this way 3-(4-chlorophenyl)-1-dimethylamino-3-phenylthio-2-propene (Z) acid oxalate (3 g) is obtained in the form of white crystals melting at 183° C.

1-(4-Chlorophenyl)-3-dimethylamino-2-propen-1-one can be obtained by the method described by H. Meerwein, W. Florian, N. Schon and G. Stopp, *Ann. Chem.* 641, 1, (1961).

EXAMPLE 40

By using a method similar to that described in Example 35, but starting from 1-(4-fluorophenyl)-3-dimethylamino-2-propen-1-one (10 g), phosphorus oxychloride (4.76 cc), thiophenol (5.57 cc) and sodium cyanoborohydride (1.92 g), a residue is obtained which is taken up in chloroform. The solution is then adjusted to pH 10 by adding a concentrated aqueous solution of sodium hydroxide. The organic phase is separated and then the aqueous phase is extracted with methylene chloride. The organic phases are collected, dried over sodium sulphate, filtered and then evaporated to dryness under reduced pressured (2.7 kPa) at 30° C. A residue is obtained which is dissolved in isopropanol (30 cc). A 3N solution (12 cc) of hydrochloric acid gas in ethyl ether is added to this solution. The solid which precipitates is separated off by filtration and recrystallised from isopropanol (30 cc). In this way 1-dimethylamino-3-(4-fluorophenyl)-3-phenylthio-2-propene (E) hydrochloride (3.3 g) is obtained in the form of a white solid melting at 160° C.

1-(4-Fluorophenyl)-3-dimethylamino-2-propen-1-one can be obtained by using the method described by H. Meerwein, W. Florian, N. Schon and G. Stopp, *Ann. Chem.* 641, 1, (1961).

EXAMPLE 41

By starting with the crystallisation mother liquors obtained in Example 40 and evaporating the solvents, a residue is obtained which is dissolved in water (50 cc). The solution obtained is made alkaline to pH 10 with a concentrated solution of sodium hydroxide. After extraction with methylene chloride, the organic phase is dried over sodium sulphate, filtered and evaporated to dryness. An orange oil is obtained which is purified by "flash" πchromatography [eluent: methylene chloride/methanol (95/5 by volume)]. Fractions 33 to 100 are concentrated under reduced pressure (2.7 kPa) at 30° C. to give a residue which is dissolved in ethanol (40 cc). A 1.1M solution (30 cc) of oxalic acid is acetone is added to this solution. The solid which precipitates is separated off by filtration and recrystallised from ethanol (40 cc). In this way 1-dimethylamino-3-(4-fluorophenylthio)-3-phenyl-2-propene (Z) oxalate (2.5 g) is obtained in the form of a white solid melting at 163° C.

EXAMPLE 42

By using a method similar to that described in Example 35, but starting from 1-(4-bromophenyl)-3-dimethylamino-2-propen-1-one (10 g), phosphorus oxychloride (3.64 g), thiophenol (4.2 cc) and sodium cyanoborohydride (1.47 g), a residue is obtained which is taken up in chloroform. The solution is adjusted to pH 10 by adding a concentrated aqueous solution of sodium hydroxide. The organic phase is separated and then the aqueous phase is extracted with methylene chloride. The organic phases are collected, dried over sodium sulphate, filtered and then evaporated to dryness under reduced pressure (2.6 kPa) at 30° C. to give a residue which is dissolved in isopropanol (30 cc). A 3N ether solution (13 cc) of hydrochloric acid gas is added to the solution obtained. The white solid which precipitates is separated off by filtration and recrystallised twice from isopropanol (40 cc). In this way 3-(4-bromophenyl)-1-dimethylamino-3-phenylthio-2-propene (E) hydrochloride (4.8 g) is obtained in the form of white crystals melting at 187° C.

1-(4-Bromophenyl)-3-dimethylamino-2-propen-1-one can be obtained by using the method of H. Meerwein, W. Florian, N. Schon and G. Stopp, *Ann. Chem.* 641, 1, (1961).

EXAMPLE 43

By starting with the crystallisation mother liquors obtained in Example 42 and evaporating the solvents, a residue is obtained which is dissolved in water (100 cc). The solution obtained is made alkaline to pH 10 by adding an aqueous solution of sodium hydroxide. After extraction with methylene chloride, the organic phase is dried over sodium sulphate, filtered and then concentrated under reduced pressure (2.7 kPa) at 30° C. A residue is obtained which is dissolved in ethanol (20 cc). A 1.7M solution (10 cc) of oxalic acid in acetone is added to this solution. The white solid which precipitates is separated off by filtration and recrystallised from ethanol (160 cc). In this way a 75/25 mixture (3.7 g) of the oxalates of 3-(4-bromophenyl)-1-dimethylamino-3-phenylthio-2-propene (Z) and of 3-(4-bromophenyl)-1-dimethylamino-3-phenylthio-2-propene (E) is obtained in the form of white crystals melting at 281° C.

EXAMPLE 44

By using a method similar to that described in Example 35, but starting from 3-dimethylaminoacrylophenone (5 g), phosphorus oxychloride (2.47 cc), 4-bromothiophenol (5.39 g) and sodium cyanoborohydride (1 g), a chestnut-coloured residue is obtained which is taken up in chloroform. The solution is made alkaline to pH 10 with an aqueous solution of sodium hydroxide. After separation of the chloroform phase, the aqueous phase is extracted with methylene chloride. The organic phases are collected, dried over sodium sulphate, filtered and then evaporated to dryness under reduced pressure (2.7 kPa) at 30° C. A residue is obtained which is dissolved in ethanol (60 cc). A 3N ether solution (7.7 cc) of hydrochloric acid gas is added to this solution. The white solid which precipitates is separated off by filtration and recrystallised from a mixture of isopropanol and methanol (60/40 by volume). In this way 3-(4-bromophenylthio)-1-dimethylamino-3-phenyl-2-propene (Z) hydrochloride (1.8 g) is obtained in the form of a white solid melting at 252° C.

EXAMPLE 45

Dimethylamine hydrochloride (139 g) and 3 Å molecular sieve (2 g) are added to a stirred solution of 3-phenyl-3-phenylthio-2-propenal (Z) (40.5 g) in methanol (370 cc) under an argon atmosphere. After 5 minutes' stirring, sodium cyanoborohydride (10.7 g) is added and stirring is continued for 18 hours. An aqueous solution (26 cc) of concentrated hydrochloric acid is then added and the mixture is concentrated to dryness under reduced pressure (2.7 kPa) at 40° C. The residue obtained is taken up in water and then washed with ethyl ether. The aqueous phase is made alkaline to pH 10 by adding a 35% strength aqueous solution of sodium hydroxide and then taken up with methylene chloride. The organic phase is separated and filtered on diatomaceous earth, washed with water (100 cc) and then dried over sodium sulphate. After filtration, the organic phase is evaporated to dryness under reduced pressure (2.7 kPa) at 40° C. A chestnut-coloured oil is thus obtained, which is purified by chromatography on silica gel [eluent: methylene chloride/methanol (90/10 by volume)], 50-cc fractions being collected. After fractions 20 to 30 have been concentrated to dryness, a residue is obtained which is dissolved in ethanol (10 cc) and ethyl ether (70 cc). A 3.5N solution (17 cc) of hydrochloric acid gas in ethyl ether is added to this solution. The precipitate formed is separated off by filtration and then recrystallised from a mixture of ethanol (38 cc) and ethyl ether (50 cc). In this way 1-dimethylamino-3-phenyl-3-phenylthio-2-propene (Z) hydrochloride (8.9 g) is obtained in the form of white crystals melting at 176° C.

3-Phenyl-3-phenylthio-2-propenal (Z) can be prepared as follows: triethylamine (9.66 cc) and then thiophenol (5.7 cc) are added at 0° C. to a solution of 3-chloro-3-phenyl-2-propenal (Z) (9.4 g) in dichloromethane (50 cc). After 14 hours' stirring at 20° C., the mixture is poured into water (50 cc); the solution is adjusted to pH 7 by adding an aqueous solution of concentrated hydrochloric acid and is then taken up with methylene chloride. The organic phase is separated, dried over sodium sulphate, filtered and then evaporated to dryness under reduced pressure (2.7 kPa) at 40° C. In this way a residue is obtained which is purified by chromatography on silica gel [eluent: hexane followed by ethyl acetate]; after elution of the nonpolar impurities with hexane (400 cc), fractions 8 to 15 produced by elution with ethyl acetate (400 cc) are combined and evaporated to dryness under reduced pressure (2.7 kPa) at 40° C. In this way 3-phenyl-3-phenylthio-2-propenal (Z) (7.8 g) is obtained in the form of a red oil with $R_f=0.9$ in thin layer chromatography on silica gel [eluent: ethyl acetate/hexane (50/50 by volume)].

3-Chloro-3-phenyl-2-propenal (Z) can be prepared by the method described by C. M. Beaton, N. B. Chapman and K. Clarke, *J. Chem. Soc. Perkin* I, 2355, (1976).

EXAMPLE 46

A solution of bromobenzene (24.8 g) in ethyl ether (120 cc) is added dropwise over approximately 1 hour to a suspension of magnesium turnings (3.85 g) in ethyl ether (100 cc). 4-Dimethylamino-1-phenyl-2-butyn-1-ol (10 g) in ethyl ether (30 cc) is added over approximately 15 minutes to the black solution obtained. The reaction mixture is then refluxed for 3 hours and 30 minutes, and then poured into a mixture of ice (400 g) and a saturated aqueous solution (200 cc) of ammonium chloride. The organic phase is separated; the aqueous phase is extracted with methylene chloride (2×200 cc); the organic phases are combined, dried over magnesium sulphate, filtered and concentrated to dryness under reduced pressure (2.7 kPa) at 40° C. The residue is purified by "flash" chromatography [eluent: methanol/ethyl acetate (60/40 by volume)], fractions 18 to 39 are combined and concentrated to dryness under reduced pressure (2.7 kPa) at 40° C. After the residue has been recrystallised from isopropyl ether, 4-dimethylamino-1,2-diphenyl-2-buten-1-ol (E) (3.9 g) is obtained in the form of white crystals melting at 113° C.

4-Dimethylamino-1-phenyl-2-butyn-1-ol can be prepared as follows: a 1.55M solution (280 cc) of n-butyl-lithium in hexane is added to a solution of N,N-dimethylpropargylamine (33.2 g) in 1,2-dimethoxyethane (400 cc) kept under a nitrogen atmosphere at a temperature in the region of −70° C. A solution of benzaldehyde (42.4 g) in 1,2-dimethoxyethane (100 cc) is added to the suspension obtained, at a temperature in the region of −30° C. The reaction mixture is stirred for 30 minutes at a temperature in the region of 0° C., and then distilled water (20 cc) is added. The suspension obtained is filtered. The solution is dried over magnesium sulphate, filtered and concentrated to dryness under reduced pressure (2.7 kPa) at 40° C. In this way, 4-dimethylamino-1-phenyl-2-butyn-1-ol (72.3 g) is obtained in the form of a yellow oil [$R_f$=0.56; thin layer chromatography on alumina gel; eluent: ethyl acetate].

EXAMPLE 47

Benzoyl chloride (4.3 g) is added to a solution of 4-dimethylamino-1,2-diphenyl-2-buten-1-ol (Z) hydrochloride (4.7 g) in anhydrous pyridine (60 cc) kept at a temperature in the region of 0° C. The reaction mixture is then stirred for 18 hours at a temperature in the region of 20° C. and then poured into a saturated aqueous solution (300 cc) of sodium bicarbonate. The mixture obtained is extracted with ethyl acetate (3×100 cc). The organic phases are combined, washed with water (2×25 cc), dried over sodium sulphate and evaporated to dryness under reduced pressure (2.7 kPa) at a temperature in the region of 40° C. The residue obtained is then dissolved in isopropanol (50 cc). This solution is heated to boiling and a solution of oxalic acid (1.4 g) in isopropanol (10 cc) is added. The product which crystallises on cooling is separated off by filtration and then washed with isopropanol (3×3 cc). By recrystallising the product obtained in this way from isopropanol (90 cc), 4-benzoyloxy-1-dimethylamino-3,4-diphenyl-2-butene (Z) oxalate (5.3 g), melting at 170° C., is obtained.

4-Dimethylamino-1,2-diphenyl-2-buten-1-ol (Z) hydrochloride can be prepared as in Example 1.

EXAMPLE 48

By proceeding as in Example 47 but starting from 4-dimethylamino-1,2-diphenyl-2-buten-1-ol (Z) hydrochloride (4.5 g), acetyl chloride (3.5 g) and oxalic acid (1.35 g), 4-acetoxy-1-dimethylamino-3,4-diphenyl-2-butene (Z) oxalate (3 g), melting at 156° C. after recrystallisation from isopropanol (300 cc) is obtained.

4-Dimethylamino-1,2-diphenyl-2-buten-1-ol (Z) hydrochloride can be prepared as in Example 1.

EXAMPLE 49

Ethyl chloroformate (1.9 cc) is added to a solution of 4-dimethylamino-1,2-diphenyl-2-buten-1-ol (Z) (4.4 g) in the form of free base in toluene (50 cc). The mixture is stirred at a temperature of 90°–95° C. for 3 hours and then cooled to ambient temperature. The precipitate formed is filtered off on a glass sinter and then washed with isopropyl ether. In this way 4-dimethylamino-1-ethoxycarbonyloxy-1,2-diphenyl-2-butene (Z) hydrochloride (3.86 g) is obtained in the form of a white solid melting at 178° C.

4-Dimethylamino-1,2-diphenyl-2-buten-1-ol (Z) can be obtained in a known manner from its hydrochloride prepared as in Example 1.

EXAMPLE 50

Crude 3-chloro-1-phenyl-1-phenylthio-1-propene (Z) (10.4 g) dissolved in ethanol (40 cc) is added slowly at 0° C. to a solution of tert-butylamine (41.6 cc) in ethanol (100 cc) and stirring is continued for 14 hours at ambient temperature (22° C.). The reaction mixture is evaporated to dryness under reduced pressure (2.7 kPa) at 30° C. In this way an orange-yellow residue is obtained which is purified by "flash" chromatography [eluent: methylene chloride/methanol (95/5 by volume)]. Fractions 21 to 60 are combined and concentrated to dryness under reduced pressure (2.7 kPa) at 30° C. A solid is obtained which is recrystallised from acetonitrile. In this way 3-phenyl-3-phenylthio-1-tert-butylamino-2-propene (Z) (1.4 g) is obtained in the form of a white solid melting at 206° C.

3-Chloro-1-phenyl-1-phenylthio-1-propene (Z) can be obtained as follows: ethyl chloroformate (9.4 cc) is added to a solution of 1-dimethylamino-3-phenyl-3-phenylthio-2-propane (Z) (17.6 g) in toluene (230 cc). The mixture is heated at 90° C. for 2 hours 30 minutes and then evaporated to dryness under reduced pressure (2.7 kPa) at 30° C. In this way a pale yellow oil (21.8 g) is obtained containing the expected 1-chloro-3-phenyl-3-phenylthio-2-propene (Z) mixed with ethyl dimethylcarbamate formed during the reaction. This crude oil is employed without further purification in subsequent syntheses.

NMR spectrum (60 MHz, CDCl$_3$): 4.5 ppm, 2H: —CH$_2$—; 6.5 ppm, 1H: —CH═; 6.9–75 ppm, 10H: aromatics.

EXAMPLE 51

A solution of 3-chloro-1-phenyl-1-phenylthio-1-propene (Z) (17.2 g) in ethanol (68 cc) is added dropwise to a 4.2N solution of ammoniacal ethanol (150 cc) cooled to 0° C. After 14 hours' stirring at ambient temperature, the reaction mixture is evaporated to dryness under reduced pressure (2.7 kPa) at 30° C. In this way a light yellow paste is obtained which is taken up in ethyl acetate (100 cc). The white solid which forms is separated off by filtration and recrystallised from methyl ethyl ketone (250 cc). In this way a mixture (3.5 g) of 75% 3-amino-1-phenyl-1-phenylthio-1-propene (Z) hydrochloride and 25% 3-amino-1-phenyl-1-phenylthio-1-propene (E) hydrochloride is obtained in the form of a white solid melting at 184° C.

EXAMPLE 52

A mixture of 4-chloro-1,2-diphenyl-1-ethoxycarbonyloxy-2-butene (Z) (0.6 g) and a 4.2N solution (6 cc)

of gaseous ammonia in ethanol is heated in an autoclave for 6 hours at 100° C. and then cooled to ambient temperature. The reaction mixture is evaporated to dryness under reduced pressure (2.7 kPa) at 30° C. and then the residue obtained is purified by chromatography on a column of silica gel [eluent: methanol/ethyl acetate (60/40 by volume)], 2 cc fractions being collected. Fractions 7 to 10 are combined and concentrated to dryness under reduced pressure (2.7 kPa) at 30° C. In this way 1-amino-3,4-diphenyl-4-ethoxycarbonyloxy-2-butene (Z) (0.1 g) is obtained in the form of a pale yellow oil [$R_f$: 0.15 ethyl acetate/methanol (40/60 by volume)].

4-Chloro-1,2-diphenyl-1-ethoxycarbonyl-2-butene (Z) can be obtained as follows: ethyl chloroformate (1.2 cc) is added to a solution of 1-dimethylamino-4-ethoxycarbonyloxy-3,4-diphenyl-2-butene (Z) in the form of free base in toluene (30 cc). The mixture is stirred for 1 hour and 30 minutes at 90° C. and then evaporated to dryness under reduced pressure (2.7 kPa) at 30° C. A residue is obtained which is chromatographed on a column of silica gel [eluent cyclohexane/ethyl acetate (50/50 by volume)], 30 cc fractions being collected. Fractions 3 to 6 are combined and concentrated under reduced pressure (2.7 kPa) at 30° C. In this way 4-chloro-1,2-diphenyl-1-ethoxycarbonyloxy-2-butene (Z) (1.56 g) is obtained in the form of a light yellow oil [$R_f$=0.5, eluent cyclohexane/ethyl acetate (50/50 by volume)].

1-Dimethylamino-4-ethoxycarbonyloxy-3,4-diphenyl-2-butene (Z) can be obtained in a known manner from its hydrochloride prepared as described in Example 49.

EXAMPLE 53

Triethylamine (1.05 cc) and 1,3-propanedithiol (0.74 cc) are added to a solution of 4-azido-1,2-diphenyl-1-ethoxycarbonyloxy-2-butene (Z) (0.5 g) in methanol (7.5 cc). The mixture is stirred under a nitrogen atmosphere for 18 hours at ambient temperature. The reaction mixture is then poured into water (10 cc), adjusted to pH 12 with an aqueous solution of 4N sodium hydroxide and then extracted 3 times with methylene chloride. The organic phase is dried over magnesium sulphate, filtered and then evaporated under reduced pressure (2.7 kPa) at 30° C. The residue obtained is purified by chromatography on silica gel [eluent: ethyl acetate/methanol (40/60 by volume)], 5 cc fractions being collected. Fractions 15 to 25 are evaporated to dryness under reduced pressure (2.7 kPa) at 30° C. In this way 1-amino-3,4-diphenyl-4-ethoxycarbonyloxy-2-butene (E) (0.168 g) is obtained in the form of a pale yellow oil [$R_f$=0.15, eluent: methanol/ethyl acetate (60/40 by volume)].

4-Azido-1,2-diphenyl-1-ethoxycarbonyloxy-2-butene (Z) can be prepared as follows: sodium azide (0.2 g) is added to a solution of 4-chloro-1,2-diphenyl-1-ethoxycarbonyloxy-2-butene (Z) (0.65 g) in N,N-dimethylformamide (6.5 cc) cooled to 0° C., and the mixture is then heated with stirring at 80° C. for 15 minutes. The reaction mixture is then cooled, water (10 cc) is added, and the mixture is extracted with methylene chloride (3×10 cc). The organic phase is dried over magnesium sulphate, filtered and then evaporated to dryness under reduced pressure (2.7 kPa) at 30° C. A residue is obtained which is chromatographed on a column of silica gel [eluent: ethyl acetate/cyclohexane (30/70 by volume)], 30 cc fractions being collected. Fractions 1 to 5 are combined and concentrated to dryness under reduced pressure (2.7 kPa) at 30° C. In this way 4-azido-1,2-diphenyl-1-ethoxycarbonyloxy-2-butene (Z) (0.54 g) is obtained in the form of a pale pink oil [$R_f$=0.7; eluent ethyl acetate/cyclohexane (30/70 by volume)].

4-Chloro-1,2-diphenyl-1-ethoxycarbonyloxy-2-butene (Z) can be obtained as in Example 52.

EXAMPLE 54

Potassium carbonate (0.1 g) is added to a solution of 1-amino-4-ethoxycarbonyloxy-3,4-diphenyl-2-butene (E) (0.02 g) in methanol (1 cc). The suspension obtained is stirred for 70 hours at a temperature in the region of 20° C. The reaction mixture is filtered and then concentrated to dryness under reduced pressure (2.7 kPa) at 40° C. The residue obtained is dissolved in methanol (0.2 cc); the solution obtained is poured onto silica gel (1 g) in a column 5 mm in diameter. It is first eluted with methanol (3 cc), the corresponding eluate is discarded, and then with methanol (2 cc): the corresponding eluate is concentrated to dryness under reduced pressure (2.7 kPa) at 40° C. In this way 4-amino-1,2-diphenyl-2-buten-1-ol (E) (0.006 g) is obtained in the form of a white powder.

NMR spectrum (250 MHz) CDCl$_3$:

| | |
|---|---|
| 3.20 ppm | (d, 2H: —CH$_2$N$\diagup\diagdown$) |
| 5.40 ppm | (s, 1H: —CHOH) |
| 6 ppm | (t, 1H: —CH=C) |
| 6.9 ppm  7.30 ppm | (m, 10H: aromatic protons) |

1-Amino-4-ethoxycarbonyloxy-3,4-diphenyl-2-butene (E) can be prepared as described in Example 53.

EXAMPLE 55

Methyl isocyanate (2.1 cc) and 4-dimethylaminopyridine (10 mg) are added to a solution of 4-dimethylamino-1,2-diphenyl-2-buten-1-ol (Z) hydrochloride (10.5 g) in chloroform (150 cc). The reaction mixture is stirred for 18 hours at a temperature in the region of 20° C. and then treated with a saturated aqueous solution (100 cc) of sodium bicarbonate. The aqueous phase is separated, washed with methylene chloride (2×50 cc) and then the organic phases are combined, washed with water (2×25 cc), dried over sodium sulphate and evaporated to dryness under reduced pressure (2.7 kPa) at a temperature in the region of 40° C. The residue obtained is then dissolved in isopropanol (100 cc); this solution is heated to boiling and a solution of oxalic acid (3.6 g) in isopropanol (50 cc) is added to it. The product which crystallises on cooling is separated off by filtration and then washed with isopropanol (3×5 cc). By recrystallisation of the product thus obtained from ethanol (150 cc), 1-dimethylamino-4-methylcarbamoyloxy-3,4-diphenyl-2-butene (Z) oxalate (9.1 g), melting at 194° C., is obtained.

4-Dimethylamino-1,2-diphenyl-2-buten-1-ol (Z) hydrochloride can be prepared as in Example 1.

EXAMPLE 56

Palladium on charcoal (10% weight/volume; 0.036 g) is added to a solution of 4-allylamino-1,2-diphenyl-2-buten-1-ol (Z) hydrochloride (0.5 g) in water (4.5 cc) and the mixture is stirred at a temperature of 100° C. under nitrogen atmosphere for 18 hours. Palladium on charcoal (10% weight/volume; 0.018 g) is then added and heating under reflux is continued for 12 hours. After cooling to ambient temperature, the catalyst is separated off by filtration and a 4N aqueous solution (5 cc) of sodium hydroxide is added to the solution, followed by sodium chloride until saturated. The aqueous phase is extracted with methylene chloride (3×20 cc). The organic phase is dried over magnesium sulphate, filtered and then evaporated to dryness under reduced pressure (2.7 kPa) at 30° C. to produce a light yellow oil which is chromatographed on a column of silica gel (eluent: methanol), 2 cc fractions being collected. Fractions 22 to 30 are combined and concentrated to dryness under reduced pressure (2.7 kPa) at 30° C. 4-Amino-1,2-diphenyl-2-buten-1-ol (Z) (0.035 g) is obtained in the form of a white solid.

NMR spectrum (250 MHz, CDCl$_3$): 3.35 ppm (m, 2H: —CH$_2$NH$_2$); 5.75 ppm (s, 1H: —CHOH—); 5.90 ppm (t, 1H: —CH=);

7.25 ppm  
7.40 ppm  } (m, 10)H:aromatic protons)

4-Allylamino-1,2-diphenyl-2-buten-1-ol (Z) can be obtained as described in Example 34.

EXAMPLE 57 m-Chloroperbenzoic acid (4.7 g) is added to a solution of 1-dimethylamino-3-phenyl-3-phenylthio-2-propene (Z) hydrochloride (6 g) in dichloromethane (68 cc), at 0° C. After 24 hours' a stirring at 20° C., additional m-chloroperbenzoic acid (4.7 g) is added and stirring is continued for 3 hours. The reaction mixture is poured into water (100 cc); the solution is adjusted to pH 10 by adding a 35% strength aqueous solution of sodium hydroxide and is taken up with methylene chloride. The organic phase is separated, dried over sodium sulphate, filtered and then evaporated to dryness under reduced pressure (2.7 kPa) at 40° C. In this way a residue is obtained which is dissolved in ethanol (10 cc). A 3N solution (6 cc) of hydrochloric acid gas in ethyl ether is added to this solution. The solid which precipitates is separated off by filtration and then recrystallised from a mixture of ethanol (60 cc) and acetonitrile (5 cc). In this way 1-dimethylamino-3-phenyl-3-phenylsulphinyl-2-propene (Z) hydrochloride (2 g) is obtained in the form of white crystals melting at 268° C. (decomposition).

1-Dimethylamino-3-phenyl-3-phenylthio-2-propene (Z form) hydrochloride can be obtained as described in Example 35.

EXAMPLE 58

By using a method similar to that described in Example 22, but starting from β-dimethylaminopropiophenone 2,4,6-triisopropylbenzenesulphonylhydrazone (10 g) and 2-fluorobenzaldehyde (2.6 cc), 4-dimethylamino-1-(2-fluorophenyl)-2-phenyl-2-buten-1-ol (Z) hydrochloride (3.5 g) is obtained in the form of a white powder melting at 175° C. after recrystallisation from a mixture (90 cc) of isopropanol and isopropyl ether (60/40 by volume).

EXAMPLE 59

By using a method similar to that described in Example 22, but starting from β-dimethylaminopropiophenone 2,4,6-triisopropylbenzenesulphonylhydrazone (20 g) and 3-bromobenzaldehyde (5.6 cc), 1-(3-bromophenyl)-4-dimethylamino-2-phenyl-2-buten-1-ol (Z) hydrochloride (11.3 g) is obtained in the form of a white solid melting at 188° C. after recrystallisation from isopropanol (200 cc).

EXAMPLE 60

By using a method similar to that described in Example 22, but starting from β-dimethylaminopropiophenone 2,4,6-triisopropylbenzenesulphonylhydrazone (20 g) and from o-tolualdehyde (5.78 g), 4-dimethylamino-1-(2-methylphenyl)-2-phenyl-2-buten-1-ol (Z) hydrochloride (10.2 g) is obtained in the form of a white powder melting at 204° C. after recrystallisation from ethanol (100 cc).

EXAMPLE 61

By using a method similar to that described in Example 22, but starting from β-dimethylaminopropiophenone 2,4,6-triisopropylbenzenesulphonylhydrazone (20 g) and from o-anisaldehyde (6.5 g), 4-dimethylamino-1-(2-methoxyphenyl)-2-phenyl-2-buten-1-ol (Z) (7.2 g) is obtained in the form of a white powder melting at 77° C. after recrystallisation from a mixture (85 cc) of petroleum ether and isopropyl ether (70/30 by volume).

EXAMPLE 62

By using a method similar to that described in Example 22, but starting from β-dimethylamino-3-methoxypropiophenone 2,4,6-triisopropylbenzenesulphonylhydrazone (21.7 g) and from benzaldehyde (5.4 cc), 4-dimethylamino-2-(3-methoxyphenyl)-1-phenyl-2-buten-1-ol (Z) hydrochloride (11.9 g) is obtained in the form of a white solid melting at 166° C. after recrystallisation from isopropanol (100 cc).

β-Dimethylamino-3-methoxypropiophenone 2,4,6-triisopropylbenzenesulphonylhydrazone can be prepared by a method similar to that described in Example 22 for the preparation of β-dimethylaminopropiophenone 2,4,6-triisopropylbenzenesulphonylhydrazone, but starting from 2,4,6-triisopropylbenzenesulphonylhydrazine (25.3 g) and β-dimethylamino-3-methoxypropiophenone hydrochloride (20.7 g). In this way β-dimethylamino-3-methoxypropiophenone 2,4,6-triisopropylbenzenesulphonylhydrazone hydrochloride (26.1 g) is obtained in the form of a white solid melting at 188° C.

β-Dimethylamino-3-methoxypropiophenone hydrochloride can be prepared by the method described in German Pat. No. 2,360,455.

EXAMPLE 63

By using a procedure similar to that described in Example 22, but starting from β-dimethylaminopropiophenone 2,4,6-triisopropylbenzenesulphonylhydrazone (20 g) and from cyclopropanecarboxaldehyde (3.37 g), an orange oil is obtained after evaporation of the organic phases to dryness under reduced pressure (2.7 kPa) at 30° C., which is purified by "flash" chromatography [eluent: ethyl acetate/methanol (8/20 by volume)]. After fractions 20 to 80 have been evaporated to dryness under reduced pressure (2.7 kPa) at 30° C., an oil is obtained. This oil is dissolved in acetone (50 cc); oxalic acid (3.93 g) dissolved in acetone (50 cc) is added to the solution obtained. The solid formed is separated off by filtration and then recrystallised from acetonitrile (80 cc). In this way 1-cyclopropyl-4-dimethylamino-2-phenyl-2-buten-1-ol (Z) oxalate (7.2 g) is obtained in the form of a white powder melting at 127° C.

Cyclopropanecarboxaldehyde can be prepared by the method described by A. J. Mancuso, D. S. Brownfair, D. Swern, *J. Org. Chem.* 23, 4148, (1979).

EXAMPLE 64

By using a method similar to that described in Example 22 but starting from β-dimethylaminopropiophenone 2,4,6-triisopropylbenzenesulphonylhydrazone (20 g) and from α-tetralone (6.4 cc), 1-(1-hydroxy-1,2,3,4-tetrahydro-1-naphthyl)-3-dimethylamino-1-phenyl-1-propene (Z) (3.8 g) is obtained in the form of a white powder melting at 108° C. after recrystallisation from a mixture (65 cc of petroleum ether and isopropanol (95/5 by volume).

EXAMPLE 65

By using a procedure similar to that described in Example 22 but starting from β-dimethylaminopropiophenone 2,4,6-triisopropylbenzenesulphonylhydrazone (20 g) and from cyclohexanone (5 cc), 1-(1-hydroxy-1-cyclohexyl)-3-dimethylamino-1-phenyl-1-propene (Z) hydrochloride (6 g) is obtained in the form of a white powder melting at 197° C. after recrystallisation from a mixture (50 cc) of isopropanol and isopropyl ether (60/40 by volume).

EXAMPLE 66

By using a method similar to that described in Example 22, but starting from β-dimethylaminopropiophenone 2,4,6-triisopropylbenzenesulphonylhydrazone (20 g) and from isobutyraldehyde (3.47 g) 1-dimethylamino-5-methyl-3-phenyl-2-hexen-4-ol (Z) hydrochloride (5.6 g) is obtained in the form of a white powder melting at 163° C. after recrystallisation from acetone (150 cc).

EXAMPLE 67

By using a method similar to that described in Example 22, but starting from α-(1-methyl-2-pyrrolidinyl)acetophenone 2,4,6-triisopropylbenzenesulphonylhydrazone (13 g) and from benzaldehyde (3.5 cc), 1,2-diphenyl-3-(1-methyl-2-pyrrolidinyl)-2-propen-1-ol (Z) hydrochloride (3.45 g) is obtained in the form of a white solid melting at 240° C. after recrystallisation from ethanol (100 cc).

α-(1-Methyl-2-pyrrolidinyl)acetophenone 2,4,6-triisopropylbenzenesulphonylhydrazone can be prepared by a method similar to that described in Example 22 for the preparation of β-dimethylaminopropiophenone 2,4,6-triisopropylbenzenesulphonylhydrazone, but starting from 2,4,6-triisopropylbenzenesulphonylhydrazine (30.6 g) and α-(1-methyl-2-pyrrolidinyl)acetophenone hydrochloride (28.3 g). In this way, α-(1-methyl-2-pyrrolidinyl)acetophenone 2,4,6-triisopropylbenzenesulphonylhydrazone hydrochloride (31.1 g) is obtained in the form a white solid melting at 210° C.

α-(1-Methyl-2-pyrrolidinyl)acetophenone hydrochloride can be prepared by the method described by A. S. Radwan, F. R. Melek, S. Negm, *J. prakt. Chem.*, (1980), 322, 475.

EXAMPLE 68

A 1.9M solution (30.4 cc) of tert-butyllithium in pentane is added to a solution of β-dimethylamino-α-methylpropiophenone 2,4,6-triisopropylbenzenesulphonylhydrazone (10.9 g) in 1,2-dimethoxyethane (109 cc), kept under nitrogen atmosphere at a temperature in the region of −75° C. Once the addition has been completed the reaction mixture is warmed slowly to 15° C. When gas evolution has stopped, the reaction mixture is cooled to a temperature in the region of −40° C. Benzaldehyde (4.2 g) is then added and stirring is continued for 20 minutes while the temperature is allowed to rise to approximately −5° C. Distilled water (50 cc), an aqueous solution (7 cc) of concentrated hydrochloric acid, and then ethyl ether (200 cc) are added in succession. The organic phase is separated and then extracted with a 4N aqueous solution of hydrochloric acid (2×25 cc). The aqueous phases are combined, made alkaline to a pH in the region of 10 with a 10N aqueous solution of sodium hydroxide and then extracted with ethyl acetate (3×150 cc). The organic phases are combined, dried over magnesium sulphate, filtered and then concentrated to dryness under reduced pressure (2.7 kPa) at 30° C. The orange oil obtained is dissolved in acetone (91 cc); a 5.6N solution (4.5 cc) of hydrochloric acid gas in ethyl ether is added to the solution obtained. The solid formed is separated off by filtration and then recrystallised from a mixture (48 cc) of isopropanol and isopropyl ether (80/20 by volume). In this way 4-dimethylamino-1,2-diphenyl-3-methyl-2-buten-1-ol (Z) hydrochloride (1.85 g) is obtained in the form of a white powder melting at 212° C.

β-Dimethylamino-α-methylpropiophenone 2,4,6-triisopropylbenzenesulphonylhydrazone can be prepared as follows: 2,4,6-triisopropylbenzenesulphonylhydrazine (23.8 g) is added to α-methyl-β-dimethylaminopropiophenone hydrochloride (16.3 g) dissolved in methylene chloride (150 cc) and acetic acid (5 cc). The solution is stirred at ambient temperature for 24 hours and is then poured into water (50 cc). The aqueous phase is extracted with methylene chloride (2×50 cc) and then the organic phases are combined, dried over magnesium sulphate, filtered and evaporated to dryness under reduced pressure (2.7 kPa) at 40° C. to give a yellow oil which is crystallised in a mixture (120 cc) of ethyl acetate and isopropyl ether (50/50 by volume). In this way β-dimethylamino-α-methylpropiophenone 2,4,6-triisopropylbenzenesulphonylhydrazone hydrochloride (16 g) is obtained in the form of a white solid melting at 147° C.

The base can be liberated from its hydrochloride as follows: the hydrochloride obtained previously is dissolved in water (100 cc) and then a 4N aqueous solution of sodium hydroxide is added to the solution obtained, up to a pH of 10, and the latter is then extracted with ethyl acetate (3×75 cc). The organic phases are combined, dried over magnesium sulphate, filtered and then evaporated to dryness under reduced pressure (2.7 kPa) at 40° C. In this way β-dimethylamino-α-methylpropiophenone 2,4,6-triisopropylbenzenesulphonylhydrazone (13 g) is obtained, as the base, in the form of a white solid melting at 113° C.

β-Dimethylamino-α-methylpropiophenone can be prepared by the method described by S. Miyano, H.

Hokari and H. Hashimoto *Bull. Chem. Soc. Japan*, 55, 534 (1982).

EXAMPLE 69

An ethanol solution (100 cc) containing 33% of methylamine is added to a solution of 4-chloro-1-ethoxycarbonyloxy-1-(3-fluorophenyl)-2-phenyl-2-butene (Z) (9.5 g) in ethanol (50 cc). After 2 hours' stirring in the absence of light, the reaction mixture is evaporated under reduced pressure (2.7 kPa) at 30° C. to give an oil. This oil is dissolved in distilled water (50 cc) and the solution obtained is made alkaline to pH 11 by adding a 4N solution of sodium hydroxide, and is then extracted with ethyl ether (3×100 cc). The organic phases are combined, dried over magnesium sulphate, filtered and then evaporated to dryness under reduced pressure (2.7 kPa) at 30° C. to give an orange oil. This oil is dissolved in ethyl acetate (40 cc) and then a 5.7N solution (5 cc) of hydrochloric acid gas in ethyl ether is added to it. The solid formed is separated off by filtration and then recrystallised from acetonitrile (20 cc). In this way 1-(3-fluorophenyl)-4-methylamino-2-phenyl-2-buten-1-ol (Z) hydrochloride (3 g) is obtained in the form of a white solid melting at 167° C.

4-Chloro-1-ethoxycarbonyloxy-1-(3-fluorophenyl)-2-phenyl-2-butene (Z) can be obtained as described in Example 52 for the preparation of 4-chloro-1,2-diphenyl-1-ethoxycarbonyloxy-2-butene, but starting from 1-dimethylamino-4-ethoxycarbonyloxy-4-(3-fluorophenyl)-3-phenyl-2-butene (Z) (26.2 g) and ethyl chloroformate (10.6 cc). After "flash" chromatography [eluent: cyclohexane/ethyl acetate (90/10 by volume)] and evaporation of fractions 12 to 18 to dryness under reduced pressure (2.7 kPa) at 30° C., 4-chloro-1-ethoxycarbonyloxy-1-(3-fluorophenyl)-2-phenyl-2-butene (Z) (21.1 g) is obtained in the form of a pale yellow oil [R$_f$=0.5; eluent: cyclohexane/ethyl acetate (50/50 by volume)].

1-Dimethylamino-4-ethoxycarbonyloxy-4-(3-fluorophenyl)-3-phenyl-2-butene (Z) hydrochloride can be obtained as described in Example 49 for the preparation of 4-dimethylamino-1-ethoxycarbonyloxy-1,2-diphenyl-2-butene (Z) hydrochloride but starting from 4-dimethylamino-4-(3-fluorophenyl)-3-phenyl-2-buten-1-ol (Z) (12.6 g) and ethyl chloroformate (5.1 cc). In this way 1-dimethylamino-4-ethoxycarbonyloxy-4-(3-fluorophenyl)-3-phenyl-2-butene (Z) hydrochloride (7.7 g) is obtained in the form of a beige solid melting at 160° C.

EXAMPLE 70

By using a method similar to that described in Example 35, but starting from 3-dimethylaminoacrylophenone (5 g), phosphorus oxychloride (2.5 cc), thiophenol (4.13 g) and sodium cyanoborohydride (1 g), and after evaporating the organic phase to dryness under reduced pressure (2.7 kPa) at 40° C., a yellow oil is obtained which is dissolved in a mixture (35 cc) of ethyl ether and ethanol (70/30 by volume). Oxalic acid (2.2 g) is added to the solution obtained. The precipitate formed is separated off by filtration and recrystallised from ethanol (60 cc). In this way 1-dimethylamino-3-(4-fluorophenylthio)-3-phenyl-2-propene (Z) oxalate (5.8 g) (containing 25% of its E isomer), is obtained in the form of a white solid melting at 133° C.

EXAMPLE 71

By using a method similar to that described in Example 35, but starting from 3-dimethylaminoacrylophenone (6.1 g), phosphorus oxychloride (3 cc), 2-chlorothiophenol (5 g) and sodium cyanoborohydride (1.3 g), and after evaporating the organic phase to dryness under reduced pressure (2.7 kPa) at 40° C., a yellow oil is obtained which is dissolved in isopropanol (20 cc). A 5.6N solution (7.8 cc) of hydrochloric acid gas in ethyl ether is added to this solution. The precipitate formed is separated off by filtration and then recrystallised from isopropanol (20 cc). In this way 3-(2-chlorophenylthio)-1-dimethylamino-3-phenyl-2-propene (Z) hydrochloride (2.5 g) is obtained in the form of a white solid melting at 162° C.

EXAMPLE 72

By using a method similar to that described in Example 35, but starting from 3-dimethylaminoacrylophenone (5 g), phosphorus oxychloride (2.5 cc), 3-chlorothiophenol (4.13 g) and sodium cyanoborohydride (1 g), and after evaporating the organic phase to dryness under reduced pressure (2.7 kPa) at 40° C., a residue is obtained which is dissolved in a mixture (20 cc) of acetone and ethyl ether (50/50 by volume). A 5.6N solution (6 cc) of hydrochloric acid gas in ethyl ether is added to this solution. The precipitate formed is separated off by filtration and then recrystallised from isopropanol (30 cc). In this way 3-(3-chlorophenylthio)-1-dimethylamino-3-phenyl-2-propene (Z) hydrochloride (2.6 g) is obtained in the form of a white solid melting at 156°–157° C.

EXAMPLE 73

By using a method similar to that described in Example 35, but starting from 3-dimethylaminoacrylophenone (5 g), phosphorus oxychloride (2.47 cc), 4-methylthiophenol (3.55 g) and sodium cyanoborohydride (1 g), and after evaporating the organic phase to dryness under reduced pressure (2.7 kPa) at 40° C., an orange oil is obtained which is dissolved in isopropanol (40 cc). A 5.6N solution (7 cc) of hydrochloric acid gas in ethyl ether is added to this solution. The precipitate formed is separated off by filtration and then recrystallised from isopropanol (40 cc). In this way 1-dimethylamino-3-(4-methylphenylthio)-3-phenyl-2-propene (Z) hydrochloride (3.3 g) is obtained in the form of a white solid melting at 197°–198° C.

EXAMPLE 74

By using a method similar to that described in Example 50, but starting from 3-chloro-1-phenyl-1-phenylthio-1-propene (Z) (45 g) and from a methanol solution (143 cc) containing 33% of methylamine, an orange oil is obtained after evaporation to dryness under reduced pressure (2.7 kPa) at 30° C., which is dissolved in ethyl acetate (150 cc). A 5.6N solution (18.5 cc) of hydrochloric acid gas in ethyl ether is added to this solution. The precipitate formed is separated off by filtration and then recrystallised from isopropanol (70 cc). In this way 1-methylamino-3-phenyl-3-phenylthio-2-propene (Z) hydrochloride (12.8 g) is obtained in the form of a white solid melting at 141° C.

EXAMPLE 75

A 1.5N solution (20 cc) of n-butyllithium in hexane is added to a solution of 3-bromo-3-(3-chlorophenyl)-1-dimethylamino-2-propene (Z) (5.1 g) in pentane (50 cc) kept under nitrogen atmosphere at a temperature in the region of −78° C. and the mixture is stirred for 25 minutes at −50° C. Benzaldehyde (4 cc) dissolved in pentane (6 cc) is then added and stirring is continued for 30 minutes while the temperature is allowed to rise to 25° C. Distilled water (80 cc) is then added followed by a 2N aqueous solution (30 cc) of hydrochloric acid. The aqueous phase is separated, washed with ethyl ether (3×25 cc), neutralised with a saturated aqueous solution of sodium bicarbonate, and then extracted with ethyl ether (3×50 cc). The organic phases are combined, dried over magnesium sulphate, filtered and concentrated to dryness under reduced pressure (2.7 kPa) at 40° C. The oil obtained is dissolved in ethanol (30 cc). A 5.7N solution (5.7 cc) of hydrochloric acid gas in ethyl ether is added to this solution. The solid formed is separated off by filtration and then recrystallised from isopropanol (80 cc). In this way 2-(3-chlorophenyl)-4-dimethylamino-1-phenyl-2-buten-1-ol (Z) hydrochloride (3.7 g) is obtained in the form of a white solid melting at 199° C.

3-Bromo-3-(3-chlorophenyl)-1-dimethylamino-2-propene (Z) can be prepared by a method similar to that described in Example 16, but starting from 1-(3-chlorophenyl)-3-dimethylamino-2-propen-1-one (44 g), phosphorus oxybromide (60 g) and sodium cyanoborohydride (7.9 g). After the reaction mixture has been evaporated to dryness under reduced pressure (2.7 kPa) at 30° C., a beige solid is obtained which is taken up in chloroform (400 cc). The suspension obtained is filtered and the filtrate is evaporated to dryness under reduced pressure (2.7 kPa) at 30° C. After the product thus obtained has been washed with isopropanol (75 cc), 3-bromo-3-(3-chlorophenyl)-1-dimethylamino-2-propene (Z) hydrobromide (46 g) is obtained in the form of a white solid melting at 146° C.

1-(3-Chlorophenyl)-3-dimethylamino-2-propen-1-one can be prepared by the method described in U.S. Pat. No. 4,209,621.

EXAMPLE 76

Using a method similar to that described in Example 75, but starting from 3-bromo-3-(3-chlorophenyl)-1-dimethylamino-2-propene (Z) (5.1 g), a 1.5M solution (15 cc) of n-butyllithium in hexane and 3,5-dichlorobenzaldehyde (5 g), 2-(3-chlorophenyl)-1-(3,5-dichlorophenyl)-4-dimethylamino-2-buten-1-ol (Z) hydrochloride (2.1 g) is obtained in the form of a white solid melting at 215° C. after recrystallisation from isopropanol (100 cc).

EXAMPLE 77

By using a procedure similar to that described in Example 75, but starting from 3-bromo-3-(3-chlorophenyl)-1-dimethylamino-2-propene (Z) (10.2 g), a 1.5M solution (40 cc) of n-butyllithium in hexane and 3-fluorobenzaldehyde (9.9 g), 2-(3-chlorophenyl)-4-dimethylamino-1-(3-fluorophenyl)-2-buten-1-ol (Z) hydrochloride (6.6 g) is obtained in the form of a white solid melting at 200° C. after recrystallisation from isopropanol (85 cc).

EXAMPLE 78

By using a method similar to that described in Example 16, but starting from 3-bromo-3-(2-chlorophenyl)-1-dimethylamino-2-propene (Z) (34 g) in crude form (containing the E-isomer), a 1.5M solution (90 cc) of n-butyllithium in hexane, and benzaldehyde (16 cc), and after purification by "flash" chromatography [eluent: ethyl acetate/methanol (50/50 by volume)] and concentration of fractions 18 to 25 to dryness under reduced pressure (2.7 kPa) at 40° C., a residue is obtained which is dissolved in ethyl acetate (20 cc). A 5.6N solution (4 cc) of hydrochloric acid gas in ethyl ether is added to this solution. The precipitate formed is separated off by filtration and then recrystallised from a mixture (70 cc) of acetonitrile and ethyl acetate (43/57 by volume). In this way 2-(2-chlorophenyl)-4-dimethylamino-1-phenyl-2-buten-1-ol (Z) hydrochloride (2.9 g) is obtained in the form of a white solid melting at 168° C.

3-Bromo-3-(2-chlorophenyl)-1-dimethylamino-2-propene (Z) can be prepared by a method similar to that described in Example 16, but starting from 1-(2-chlorophenyl)-3-dimethylamino-2-propen-1-one (35.2 g), phosphorus oxybromide (48.4 g) and sodium cyanoborohydride (6.35 g). After the reaction mixture has been evaporated to dryness under reduced pressure (2.7 kPa) at 30° C., a solid is obtained which is taken up in chloroform (400 cc). The suspension obtained is filtered. Distilled water (100 cc) is added to the filtrate and separated off. The aqueous phase is made alkaline to pH 9 with a concentrated aqueous solution of sodium hydroxide and is then extracted with chloroform (2×100 cc). The chloroform phases are combined, dried over magnesium sulphate, filtered and then evaporated to dryness under reduced pressure (2.7 kPa) at 30° C. In this way a mixture (34 g) of the Z and E isomers of 3-bromo-3-(2-chlorophenyl)-1-dimethylamino-2-propene is obtained in the form of a brown oil [$R_f$=0.68; eluent: dichloromethane/methanol (95/5 by volume)].

1-(2-Chlorophenyl)-3-dimethylamino-2-propen-1-one can be prepared by the method described in U.S. Pat. No. 4,209,621.

EXAMPLE 79

Triethylamine (60 cc) and 1,3-propanedithiol (43 cc) are added to a solution of 4-azido-1,2-diphenyl-2-buten-1-ol (22.7 g; mixture of 75% of Z isomer and 25% of E isomer) in methanol (370 cc). The mixture is stirred under nitrogen atmosphere for 20 hours at a temperature in the region of 20° C. and is then poured into distilled water (600 cc). The mixture is adjusted to pH 12 with a 10N aqueous solution of sodium hydroxide and then extracted with methylene chloride (3×500 cc). The organic phase is dried over magnesium sulphate, filtered and then concentrated to dryness under reduced pressure (2.7 kPa) at 30° C. The oil obtained is stirred with methylene chloride and the precipitate formed is separated off by filtration. The filtrate obtained is concentrated to dryness under reduced pressure (2.7 kPa) at 30° C. to give a yellow oil which is purified by chromatography on silica gel [eluent: methanol/ethyl acetate/11N aqueous ammonia (60/38/2 by volume)]. Elution is first carried out with 460 cc of eluent; the corresponding eluate is discarded. Elution then continues with 360 cc of eluent; the corresponding eluate is evaporated to dryness under reduced pressure (2.7 kPa) at 30° C. to give a yellow solid which is dissolved in a mixture (130 cc) of ethanol and ethyl ether (25/75 by volume). A 3.5N solution (4.8 cc) of hydrochloric acid gas in ethyl ether is added to the solution obtained. The white solid formed is separated off by filtration and then recrystallised from a mixture of ethanol (11 cc) and isopropyl ether (16 cc). In this way 4-amino-1,2-diphenyl-2-buten-1-ol (Z) hydrochloride (1.88 g) is obtained in the form of a white powder melting at 180° C.

4-Azido-1,2-diphenyl-2-buten-1-ol (mixture of 75% of Z isomer and 25% of E isomer) can be prepared as follows: potassium carbonate (117 g) is added to a solution of 4-azido-1,2-diphenyl-1-ethoxycarbonyloxy-2-butene (Z) (28.5 g) prepared as described in Example 53, in methanol (300 cc). The mixture is stirred for 16 hours in the absence of light at a temperature in the region of 20° C., and is then filtered. The filtrate is concentrated to dryness under reduced pressure (2.7 kPa) at 30° C. The oil obtained is dissolved in methylene chloride (300 cc) and then washed with distilled water (200 cc). The aqueous phase is adjusted to pH 7 by adding a 2N aqueous solution of hydrochloric acid and then extracted with methylene chloride (2×300 cc). The organic phases are combined, dried over magnesium sulphate, filtered and then concentrated to dryness under reduced pressure (2.7 kPa) at 30° C. In this way 4-azido-1,2-diphenyl-2-buten-1-ol (21.77 g) (mixture of 75% of Z isomer and 25% of E isomer) is obtained in the form of a pale yellow oil [$R_f$=0.6; eluent: cyclohexane/ethyl acetate (70/30 by volume)].

The present invention also relates to the medicaments consisting of a product of general formula (I) in free form or in the form of a salt of addition with a pharmaceutically acceptable acid, in a pure state or in the form of a composition in which it is associated with any other pharmaceutically compatible product, which may be inert or physiologically active. The medicaments according to the invention may be administered by oral, parenteral or rectal route.

As solid compositions for oral administration use may be made of tablets, pills, powders (particularly in gelatin capsules or cachets) or granules. In these compositions the active product according to the invention is mixed with one or more inert diluents such as starch, cellulose, sucrose, lactose or silica. These compositions may also contain substances other than diluents, for example one or more lubricants such as magnesium stearate or talc, a colorant, a coating (coated pills) or a varnish.

As liquid compositions for oral administration, use may be made of solutions, suspensions, emulsions, syrups and elixirs which are pharmaceutically acceptable and contain inert diluents such as water, ethanol, glycerol, vegetable oils or paraffin oils. These compositions may also contain substances other than the diluents, for example wetting agents, sweeteners, thickeners, flavourings or stabilisers.

The sterile compositions for parenteral administration may preferably be aqueous or non-aqueous solutions, suspensions or emulsions. As a solvent or vehicle, use may be made of water, propylene glycol, a polyethylene glycol, vegetable oils, in particular olive oil, injectable organic esters, for example ethyl oleate or other suitable organic solvents. These compositions may also contain adjuvants in particular wetting agents, isotonising agents, emulsifiers, dispersants and stabilisers. The sterilisation may be carried out in various ways, for example by asepticising filtration, by incorporating sterilising agents in the composition, by irradiation or by heating. They may also be prepared in the form of solid sterile compositions which may be dissolved at the time of use in an injectable sterile medium.

The compositions for rectal administration are suppositories or rectal capsules, which, in addition to the active product, contain excipients such as cocoa butter, semi-synthetic glycerides or polyethylene glycols.

In human therapy the products according to the invention are especially useful in the treatment of the syndromes of various depressive states and of psychasthenic states. The dosages depend on the effect which is required and on the duration of the treatment; they are generally between 25 and 250 mg per day by oral, intramuscular or intravenous route for an adult, in one or more doses.

In general, the medical practitioner will determine the dosage which he or she considers the most appropriate as a function of the age, weight and all the other factors pertaining to the individual to be treated.

The following examples, given without implying a restriction, illustrate the compositions according to the invention.

EXAMPLE A

Tablets containing a 25 mg dose of the active product and having the following composition are prepared according to the usual method:

| | |
|---|---|
| 4-Dimethylamino-1,2-diphenyl-2-buten-1-ol (Z) hydrochloride | 32 mg |
| Starch | 60 mg |
| Lactose | 50 mg |
| Magnesium stearate | 2 mg |

EXAMPLE B

An injectable solution containing 25 mg of active product and having the following composition is prepared:

| | |
|---|---|
| 4-Methylamino-1,2-diphenyl-2-buten-1-ol (Z) | 25 mg |
| 1 N Hydrochloric acid | 0.1 cc |
| Injectable solution q.s. | 2 cc |

We claim:

1. Process for the preparation of a 3-phenyl-2-propeneamine of the formula:

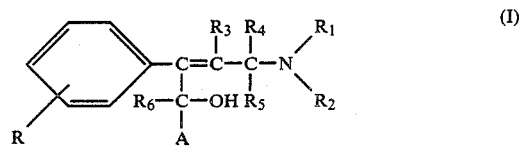

in which
R denotes hydrogen, halogen, alkyl, alkyloxy, alkylthio, amino, alkylamino, dialkylamino or trifluoromethyl;

$R_3$ denotes hydrogen or alkyl;

either $R_4$ and $R_5$ each denote hydrogen and $R_1$ and $R_2$, which are identical or different, each denote hydrogen or alkyl which is unsubstituted or substituted by alkenyl of 2 to 4 carbon atoms, $R_1$ and $R_2$ not simultaneously denoting hydrogen, or $R_1$ and $R_2$ form together with the nitrogen atom to which they are linked denote a saturated heterocyclic radical of 4 to 7 ring atoms optionally containing another heteroatom such as oxygen, sulphur or nitrogen which is unsubstituted or substituted by alkyl;

or $R_4$ denotes hydrogen, $R_1$ denotes hydrogen or alkyl and $R_2$ and $R_5$ together form an alkylene radical of 3 or 4 carbon atoms;

and A denotes alkyl or phenyl which is unsubstituted or substituted by one or two substituents chosen from halogen, alkyl, alkyloxy, alkylthio, amino, alkylamino, dialkylamino, nitro and trifluoromethyl or A denotes pyridyl, benzyl or cycloalkyl of 3 to 6 carbon atoms; and $R_6$ denotes hydrogen or alkyl, the aforesaid alkyl radicals and alkyl parts containing 1 to 4 carbon atoms each as a straight or branched chain, in the Z-configuration;

which comprises reacting a compound of formula:

$$A\!-\!CO\!-\!R_6 \qquad (III)$$

in which A and $R_6$ are as defined above, with a carbanion of formula:

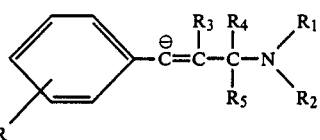

in which the symbols are as defined above, and isolating the product obtained and optionally converting it into a pharmaceutically acceptable salt.

* * * * *